(12) United States Patent
Ominami et al.

(10) Patent No.: US 10,241,062 B2
(45) Date of Patent: Mar. 26, 2019

(54) CHARGED PARTICLE BEAM DEVICE, SAMPLE OBSERVATION METHOD, SAMPLE PLATFORM, OBSERVATION SYSTEM, AND LIGHT EMITTING MEMBER

(71) Applicant: Hitachi High-Technologies Corporation, Minato-ku, Tokyo (JP)

(72) Inventors: Yusuke Ominami, Tokyo (JP); Mitsugu Sato, Tokyo (JP); Kenko Uchida, Tokyo (JP); Sadamitsu Aso, Tokyo (JP); Taku Sakazume, Tokyo (JP); Hideo Morishita, Tokyo (JP); Sukehiro Ito, Tokyo (JP); Takashi Ohshima, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 59 days.

(21) Appl. No.: 14/774,367

(22) PCT Filed: Jan. 22, 2014

(86) PCT No.: PCT/JP2014/051177
§ 371 (c)(1),
(2) Date: Sep. 10, 2015

(87) PCT Pub. No.: WO2014/141744
PCT Pub. Date: Sep. 18, 2014

(65) Prior Publication Data
US 2016/0025659 A1    Jan. 28, 2016

(30) Foreign Application Priority Data

Mar. 13, 2013   (JP) ................................. 2013-049825

(51) Int. Cl.
*H01J 37/20*    (2006.01)
*H01J 37/28*    (2006.01)
(Continued)

(52) U.S. Cl.
CPC ..... *G01N 23/2251* (2013.01); *G01N 23/2204* (2013.01); *H01J 37/20* (2013.01);
(Continued)

(58) Field of Classification Search
CPC . G01N 23/2251; G01N 23/2204; H01J 37/20; H01J 37/244; H01J 37/28
See application file for complete search history.

(56) References Cited

U.S. PATENT DOCUMENTS 9,368,324 B2 *   6/2016  Li ............................ H01J 37/28
2004/0238752 A1  12/2004 Tanba et al.
(Continued)

FOREIGN PATENT DOCUMENTS

CN   102384922 A   3/2012
CN   102645423 A   8/2012
(Continued)

OTHER PUBLICATIONS

International Search Report (PCT/ISA/210) dated Mar. 4, 2014 with English-language translation (three (3) pages).
(Continued)

*Primary Examiner* — Nicole M Ippolito
*Assistant Examiner* — Sean M Luck
(74) *Attorney, Agent, or Firm* — Crowell & Moring LLP

(57) ABSTRACT

The purpose of the present invention is to eliminate the effort in placement and extraction of samples in observations using transmitted charged particles. A charged particle beam device (601) is characterized by having: a charged particle optical lens tube that irradiates a sample (6) with a primary charged particle beam; a sample stage on which a light emitting member (500) that emits light because of charged particles that have come by transmission internally in the sample (6) or scattering therefrom or a sample platform (600) having the light emitting member (500) is attachably (Continued)

and detachably disposed; and a detector (503) that detects the light emitted by the light emitting member.

23 Claims, 27 Drawing Sheets

(51) Int. Cl.
*H01J 37/244* (2006.01)
*G01N 23/22* (2018.01)
*G01N 23/2251* (2018.01)
*G01N 23/2204* (2018.01)

(52) U.S. Cl.
CPC ............ *H01J 37/244* (2013.01); *H01J 37/28* (2013.01); *H01J 2237/2003* (2013.01); *H01J 2237/2443* (2013.01); *H01J 2237/2445* (2013.01); *H01J 2237/24455* (2013.01); *H01J 2237/2605* (2013.01)

(56) References Cited

U.S. PATENT DOCUMENTS

| | | | |
|---|---|---|---|
| 2005/0173632 A1 | 8/2005 | Behar et al. | |
| 2007/0023655 A1* | 2/2007 | Nishikata | H01J 37/228 250/310 |
| 2007/0145268 A1 | 6/2007 | Chao et al. | |
| 2008/0308731 A1 | 12/2008 | Nishiyama et al. | |
| 2009/0101817 A1* | 4/2009 | Ohshima | H01J 37/244 250/310 |
| 2011/0220793 A1* | 9/2011 | Thomas | H01J 37/20 250/307 |
| 2011/0278451 A1 | 11/2011 | Tiemeijer et al. | |
| 2011/0284745 A1* | 11/2011 | Nishiyama | G01N 23/2204 250/307 |
| 2011/0291010 A1* | 12/2011 | Katane | H01J 37/244 250/310 |
| 2012/0049060 A1 | 3/2012 | Luecken et al. | |
| 2012/0193530 A1 | 8/2012 | Parker et al. | |
| 2013/0051656 A1 | 2/2013 | Ito et al. | |
| 2013/0221217 A1 | 8/2013 | Shiono et al. | |
| 2014/0123898 A1 | 5/2014 | Nomaguchi et al. | |

FOREIGN PATENT DOCUMENTS

| | | | |
|---|---|---|---|
| CN | 102954975 A | 3/2013 | |
| EP | 2 560 185 A2 | 2/2013 | |
| EP | 2 924 706 A1 | 9/2015 | |
| JP | 58-148654 U | 10/1983 | |
| JP | 10-283978 A | 10/1998 | |
| JP | 11-14909 A | 1/1999 | |
| JP | 2005-529341 A | 9/2005 | |
| JP | 2007-165283 A | 6/2007 | |
| JP | 2008-210765 A | 9/2008 | |
| JP | 2013-20918 A | 1/2013 | |
| WO | WO 90/03844 A1 | 4/1990 | |
| WO | WO 2012/046396 A1 | 4/2012 | |

OTHER PUBLICATIONS

Extended European Search Report issued in counterpart European Application No. 14762260.9 dated Nov. 11, 2016 (10 pages).
Wang et al., "Transparent Garnet Ceramic Scintillators for Gamma-ray Detection", Hard X-Ray, Gamma Ray, and Neutron Detector Physics XIV, Proc. of SPIE, vol. 8507, 2012, pp. 850717-1-850717-8.
Chinese Office Action issued in counterpart Chinese Application No. 201480013221.0 dated Jul. 7, 2016 with English translation (20 pages).
Chinese Office Action issued in counterpart Chinese Application No. 201480013221.0 dated Nov. 16, 2016 with English translation (17 pages).
Chinese Office Action issued in counterpart Chinese Application No. 201480013221.0 dated Mar. 17, 2017 (3 pages).
Japanese-language Office Action issued in counterpart Japanese Application No. 2018-055588 dated Dec. 11, 2018 with English translation (14 pages).

\* cited by examiner

[Fig. 1]
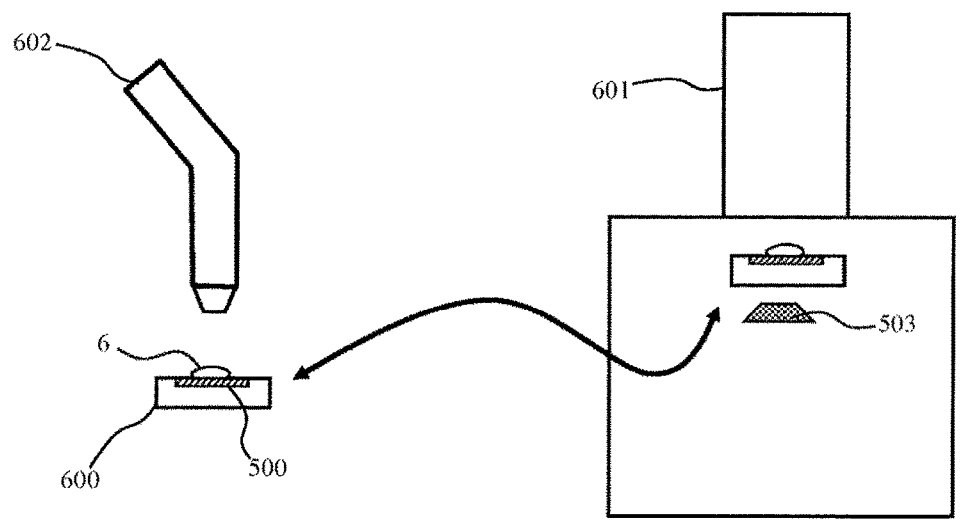
[Fig. 2]
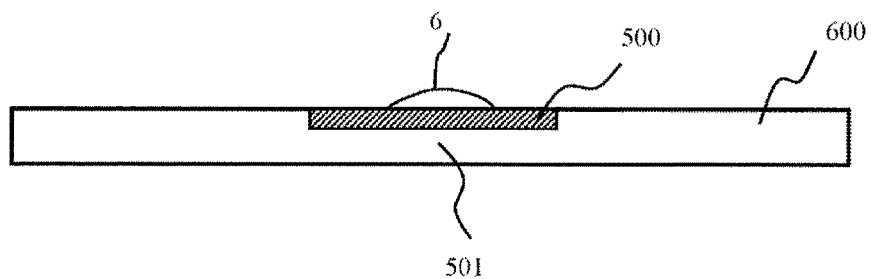

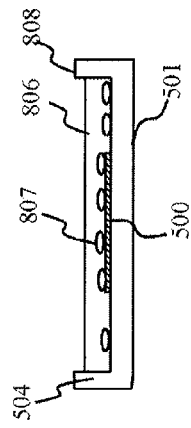
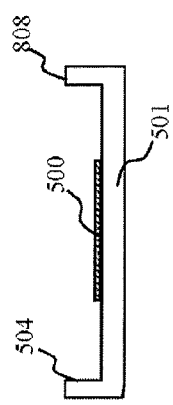
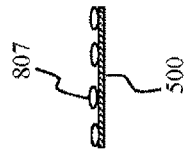
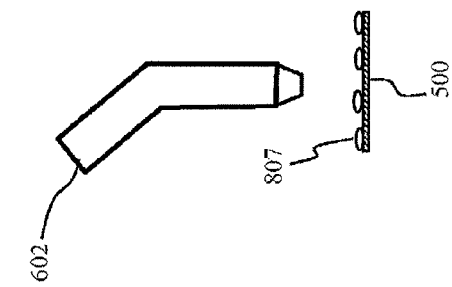

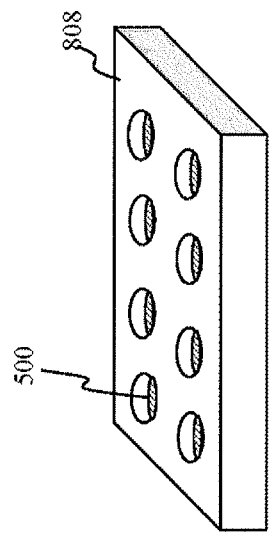
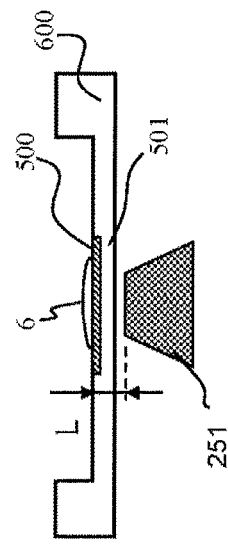
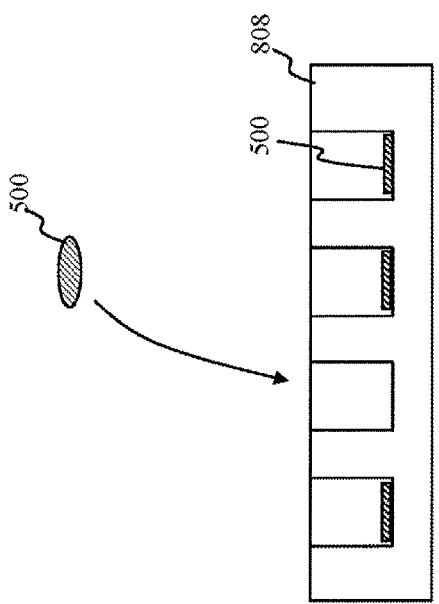
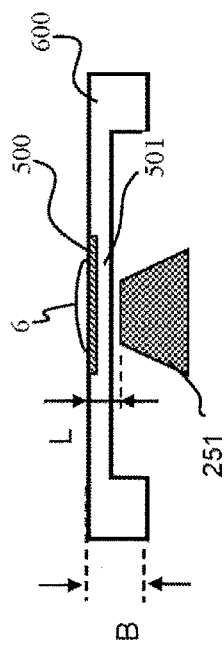

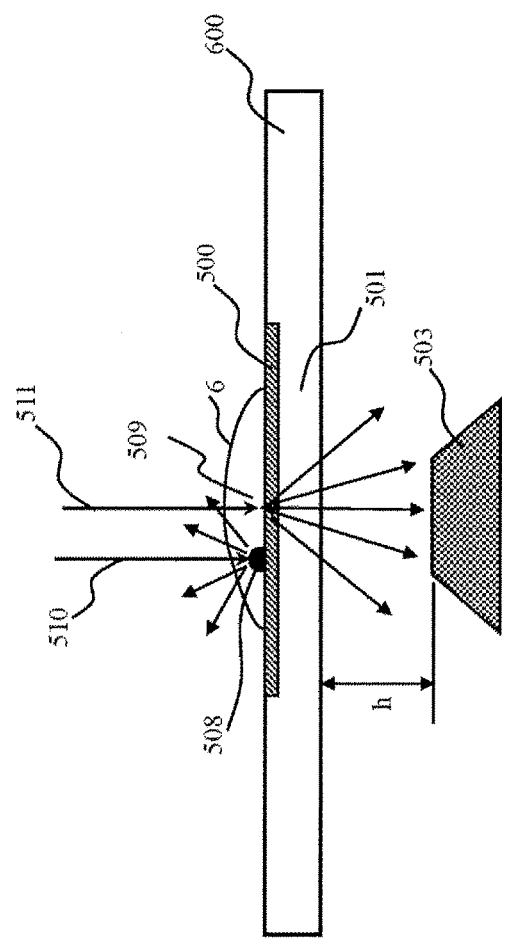
[Fig. 13]

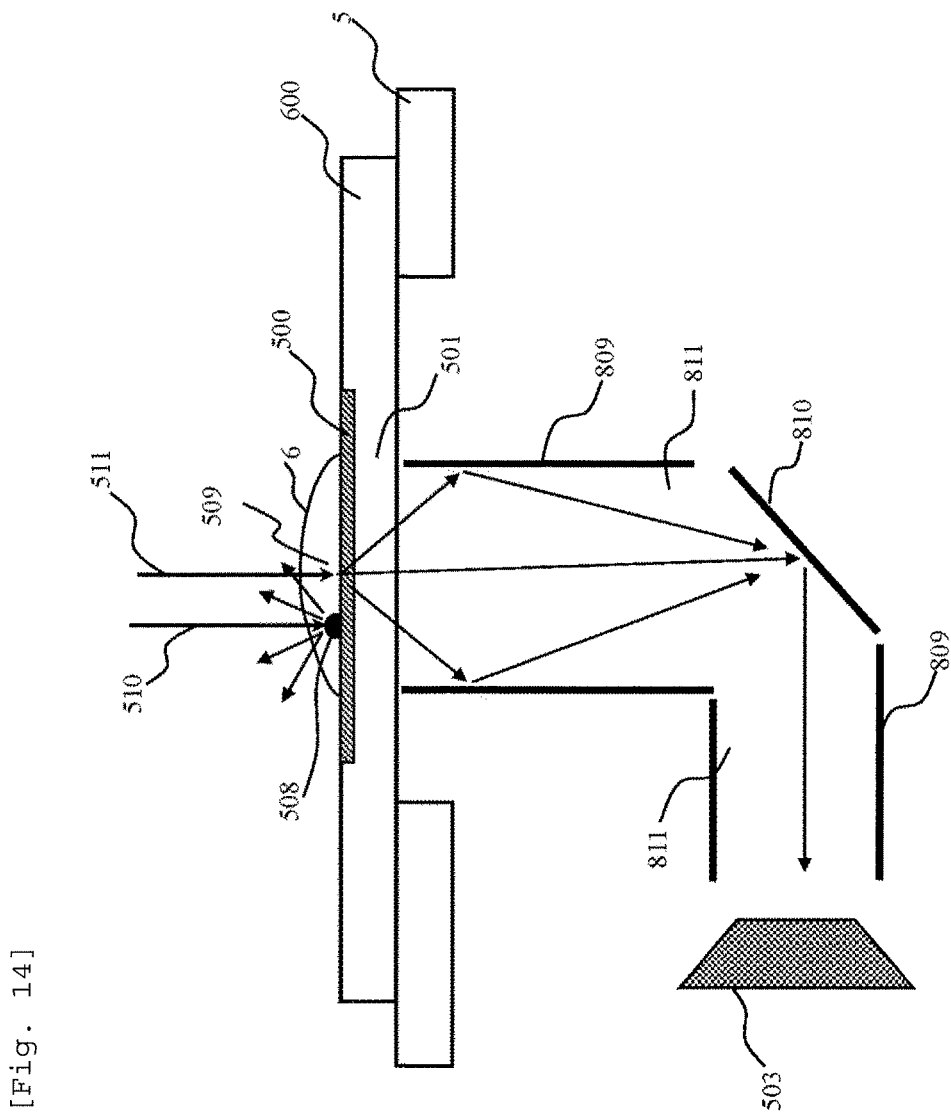
[Fig. 14]

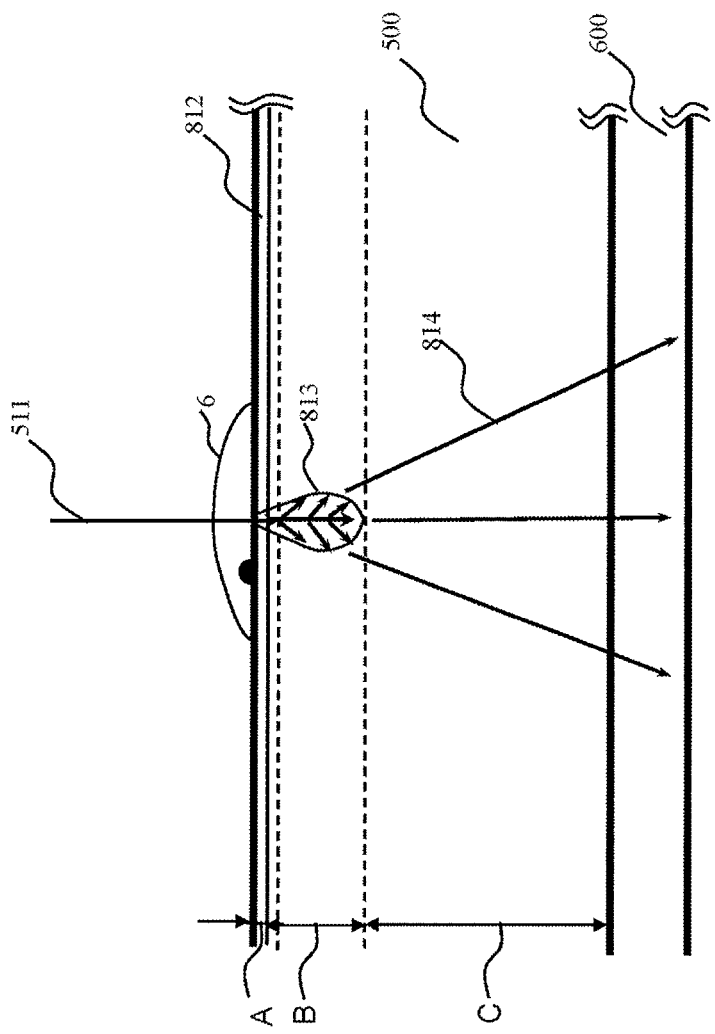
[Fig. 15]

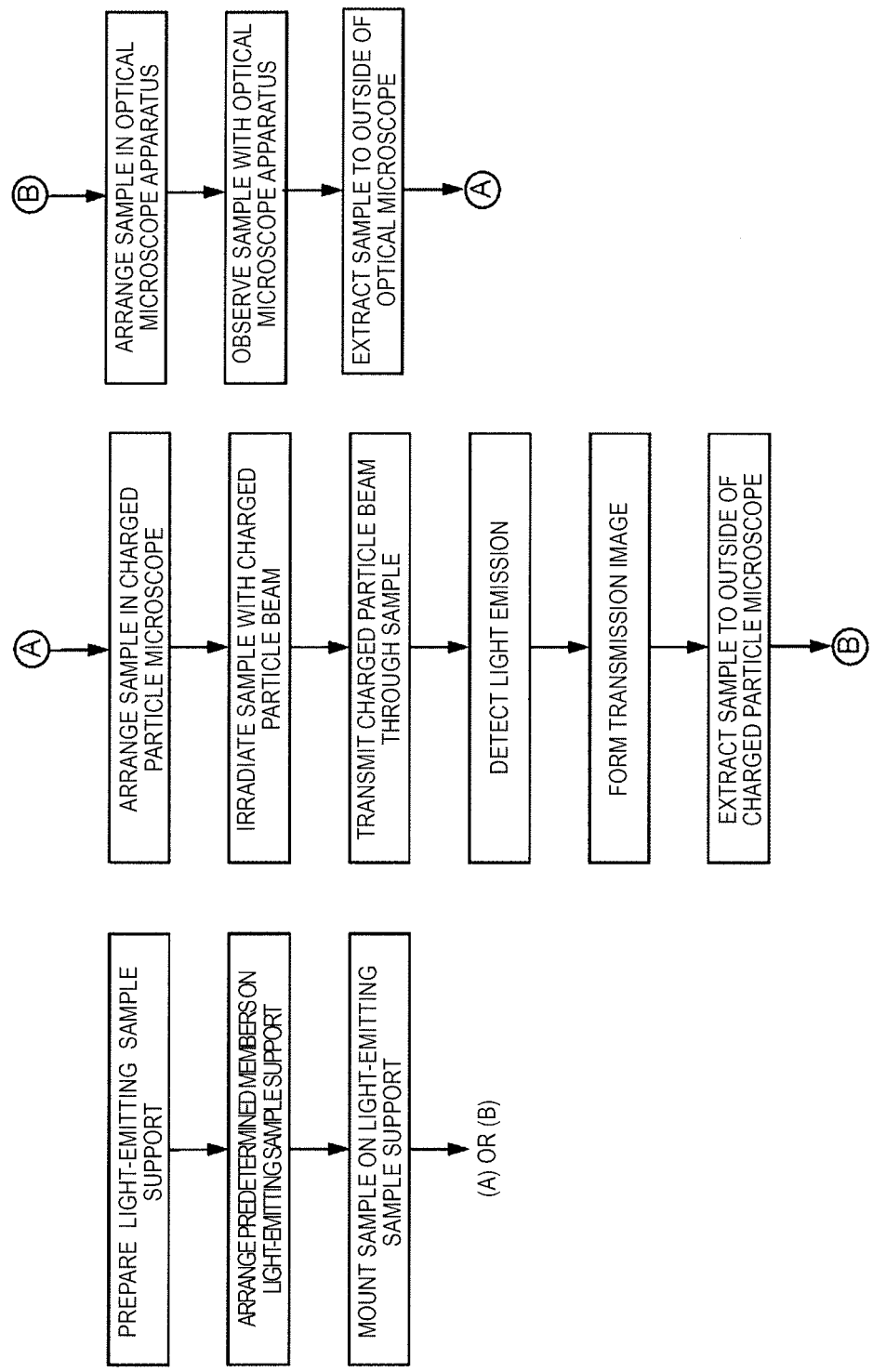
[Fig. 16]

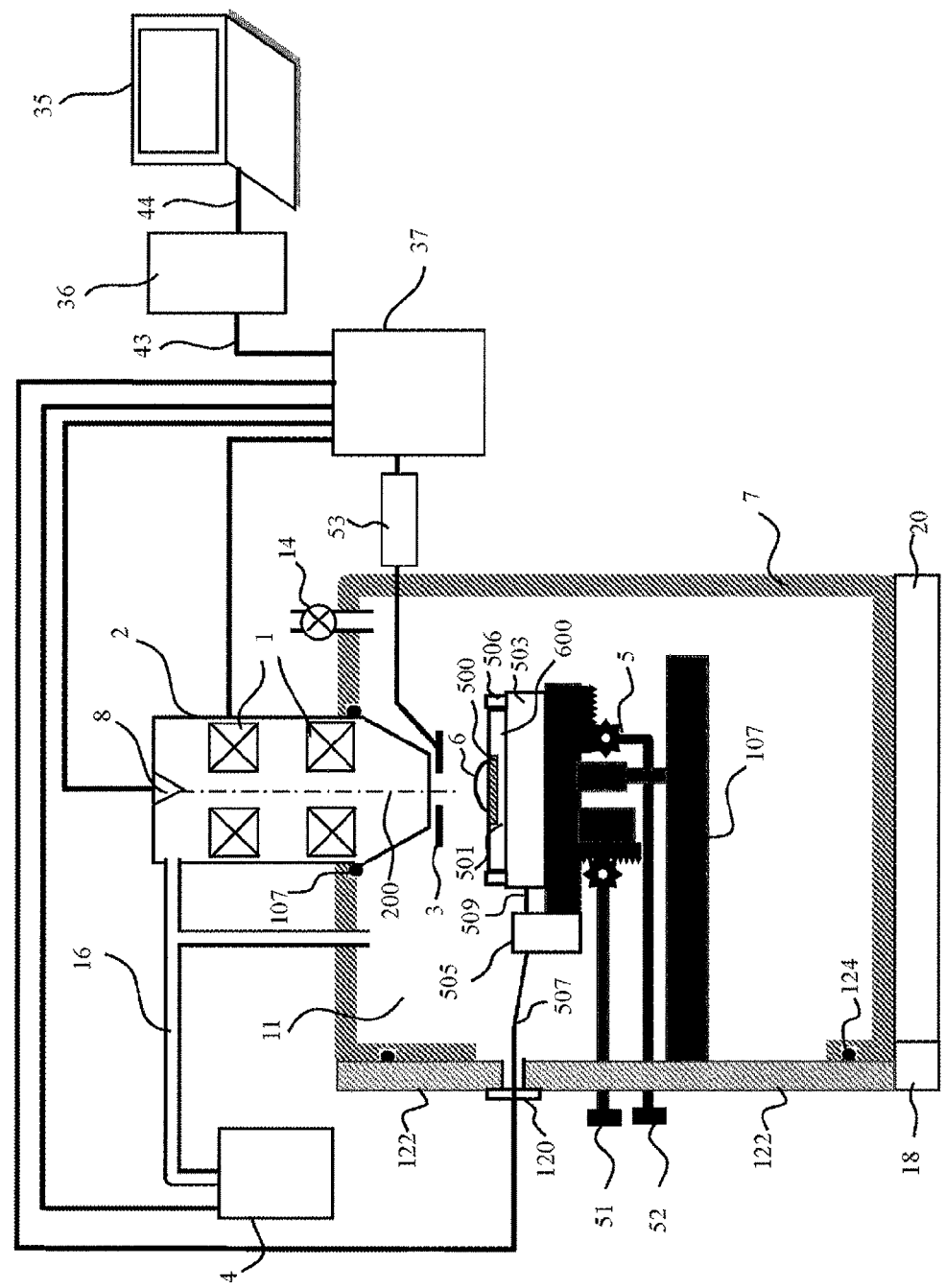
[Fig. 17]

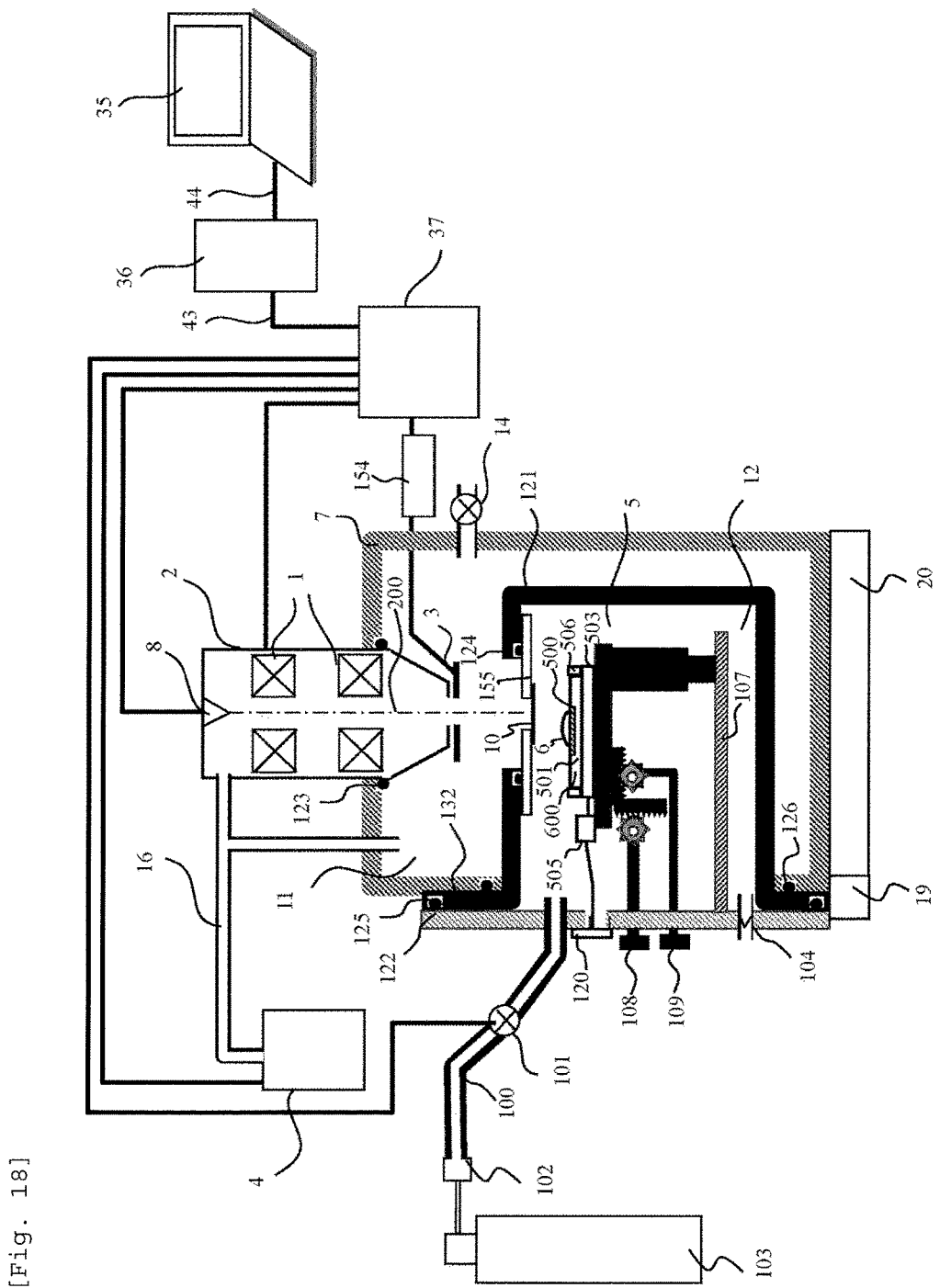
[Fig. 18]

[Fig. 19]
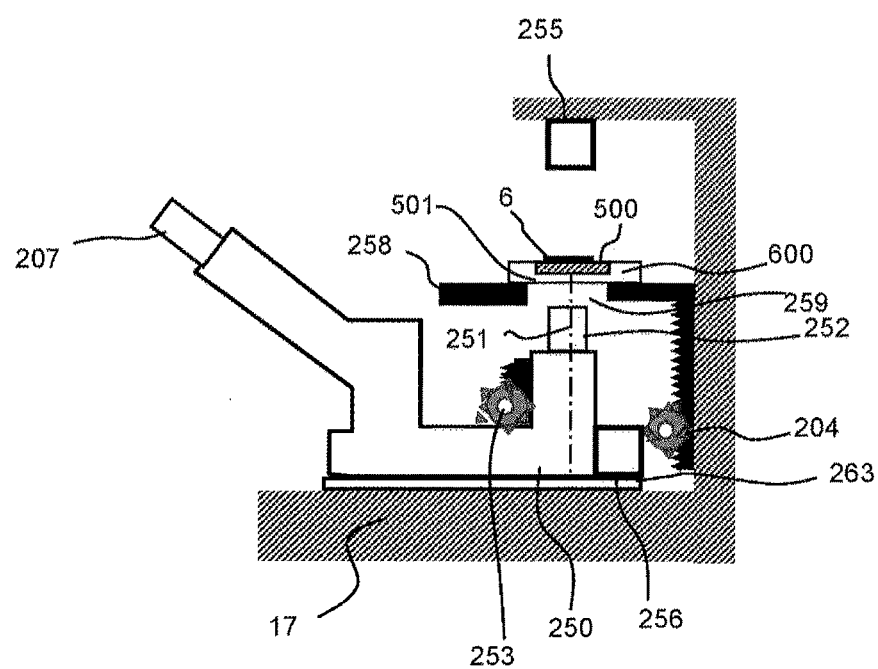

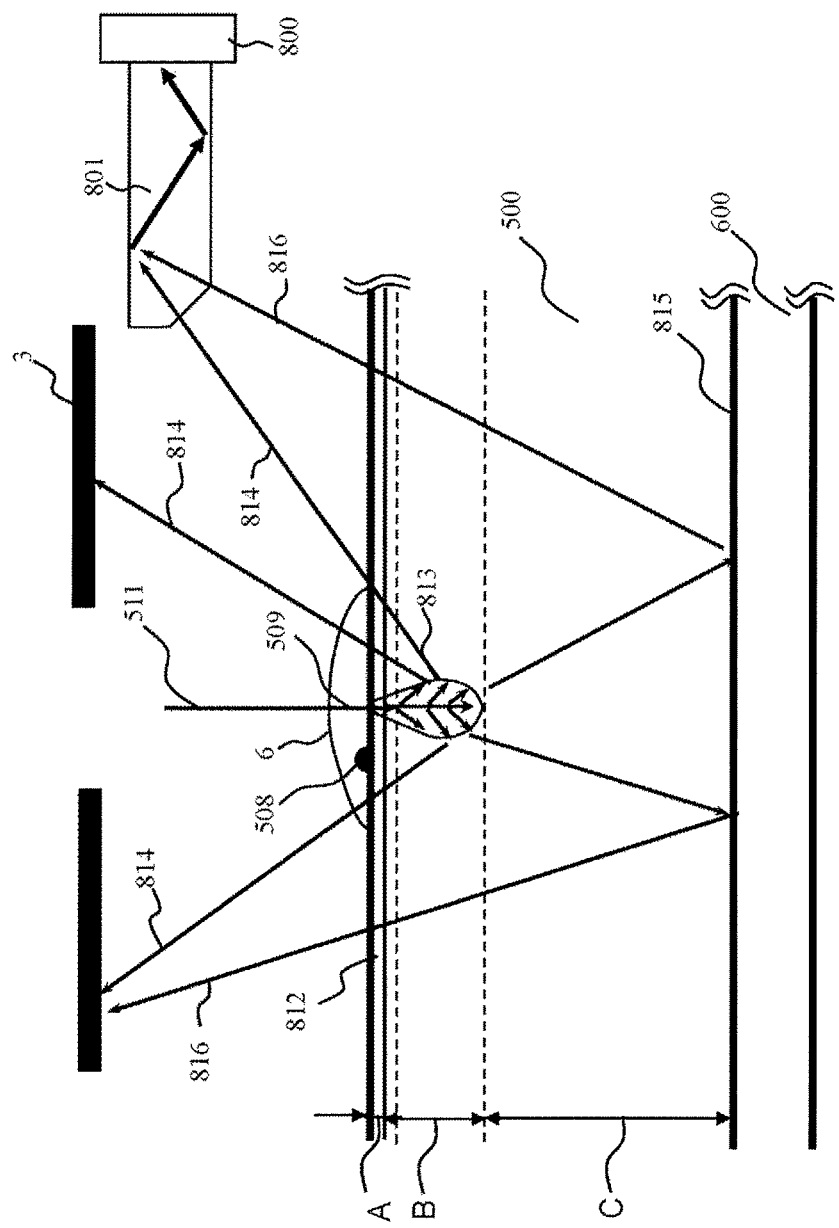
[Fig. 20]

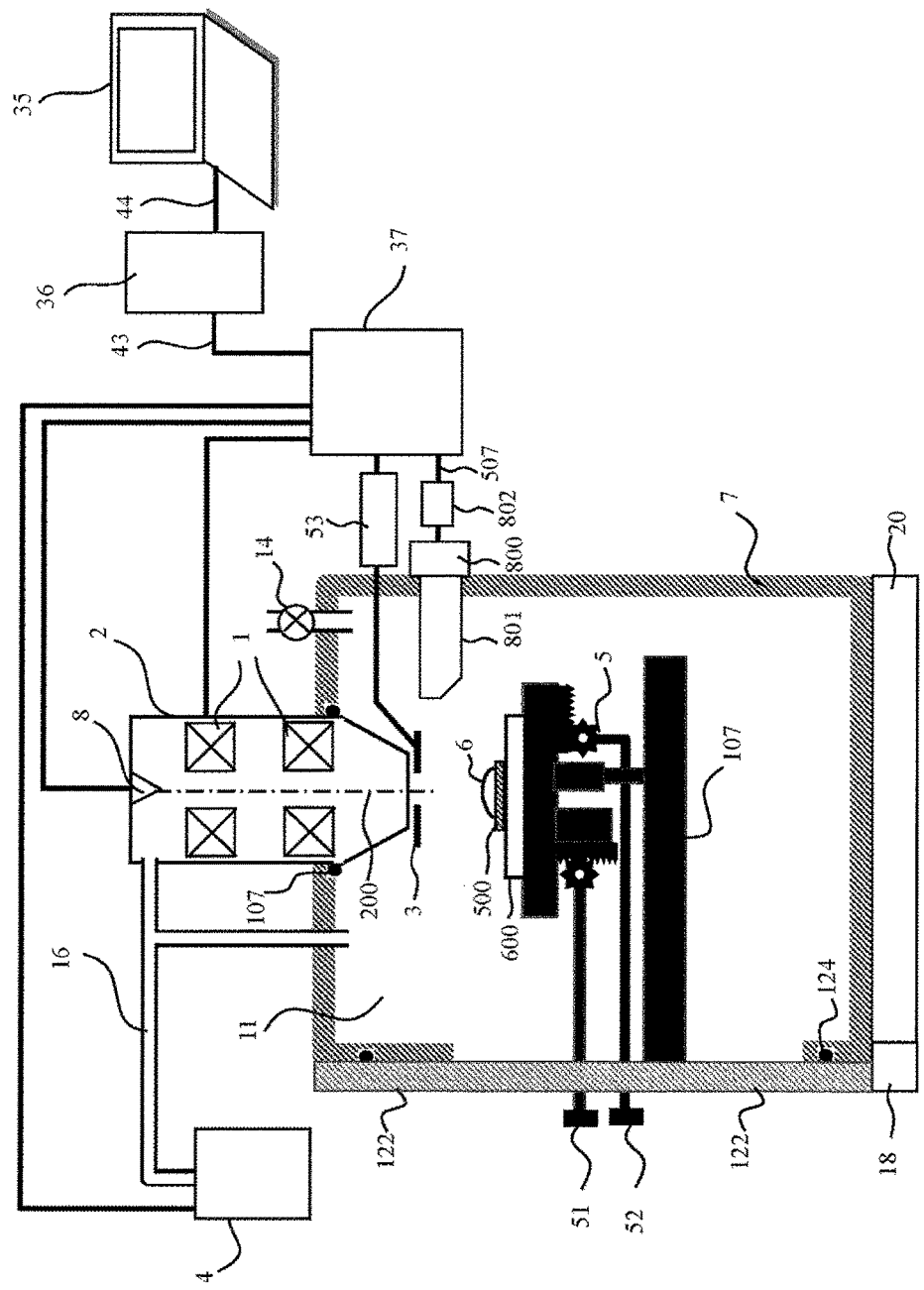
[Fig. 21]

[Fig. 23]
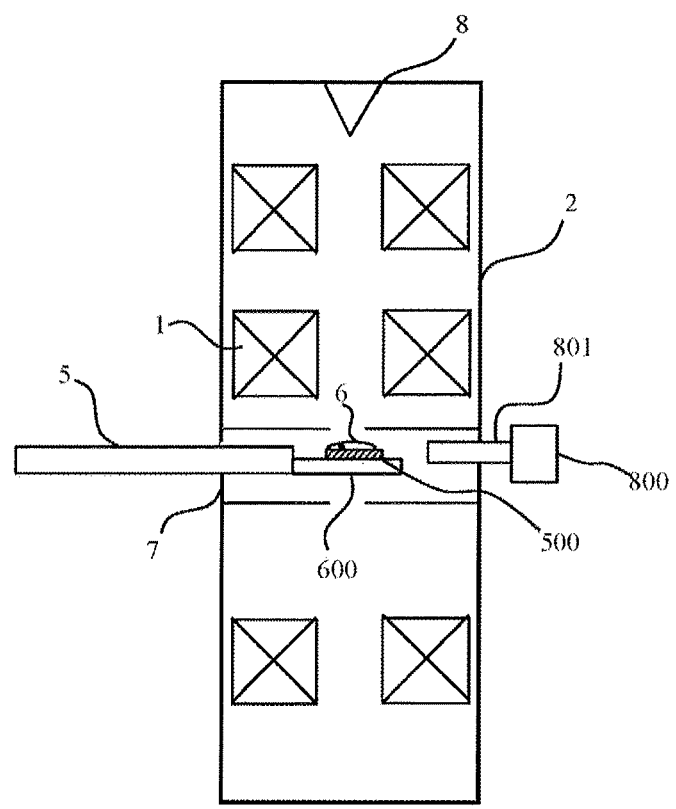

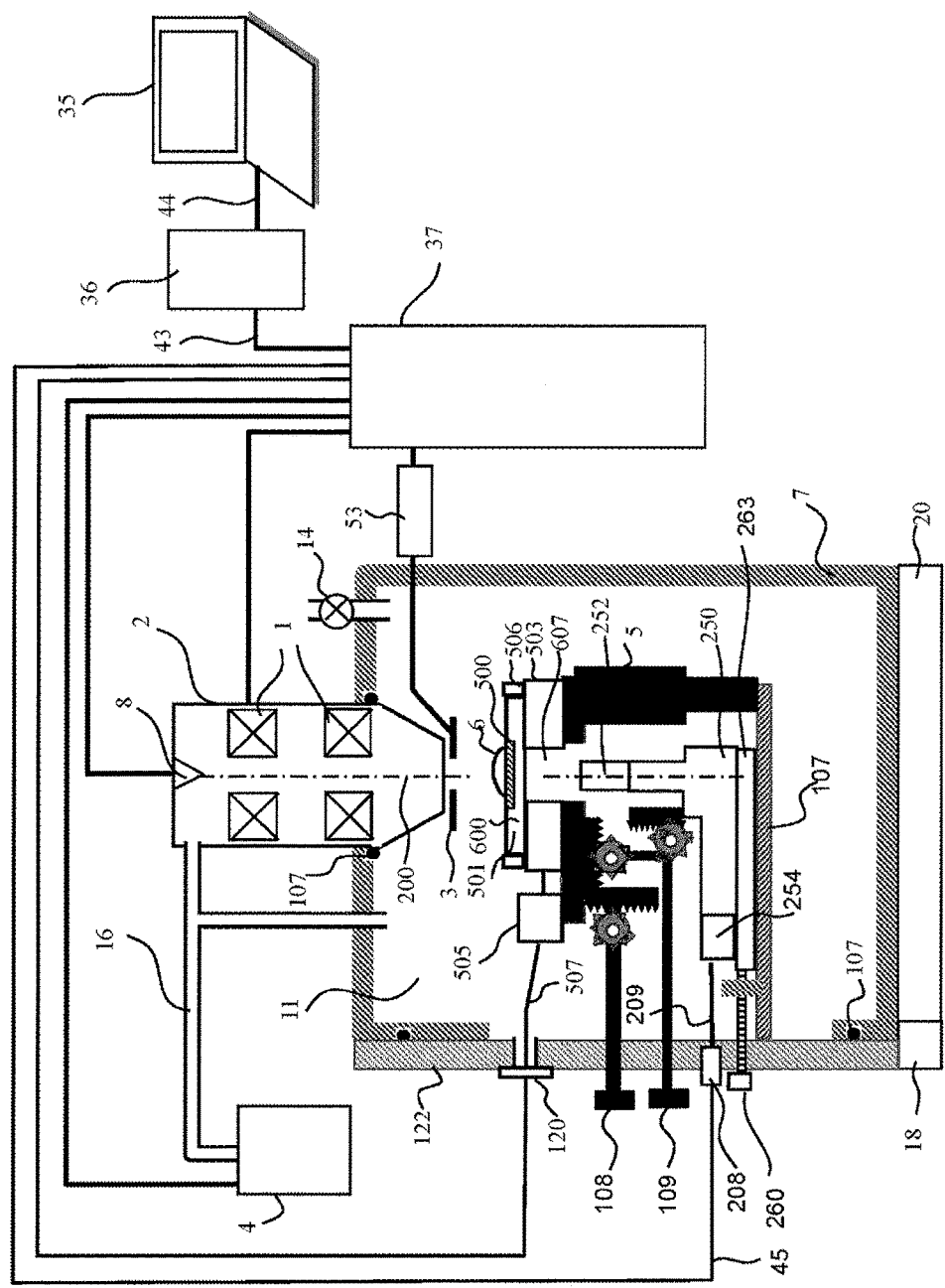
[Fig. 24]

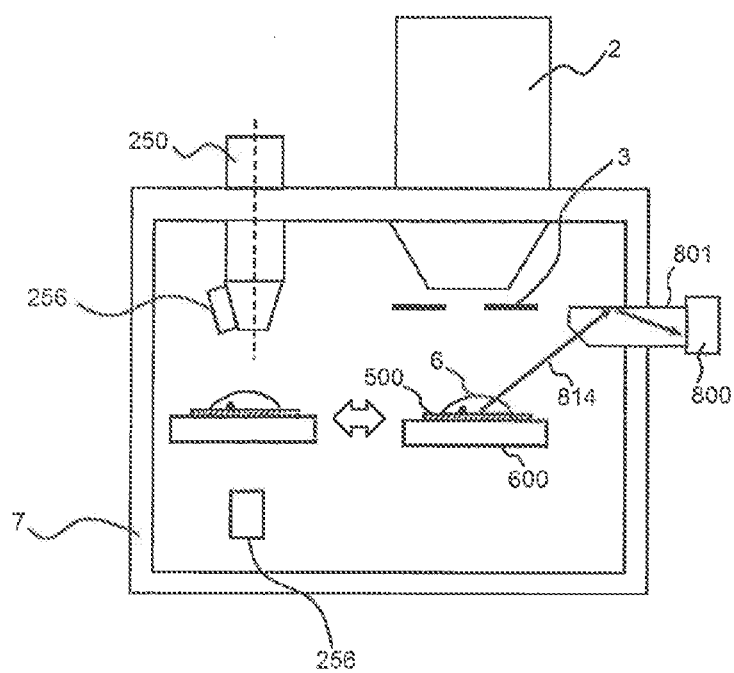
[Fig. 26]

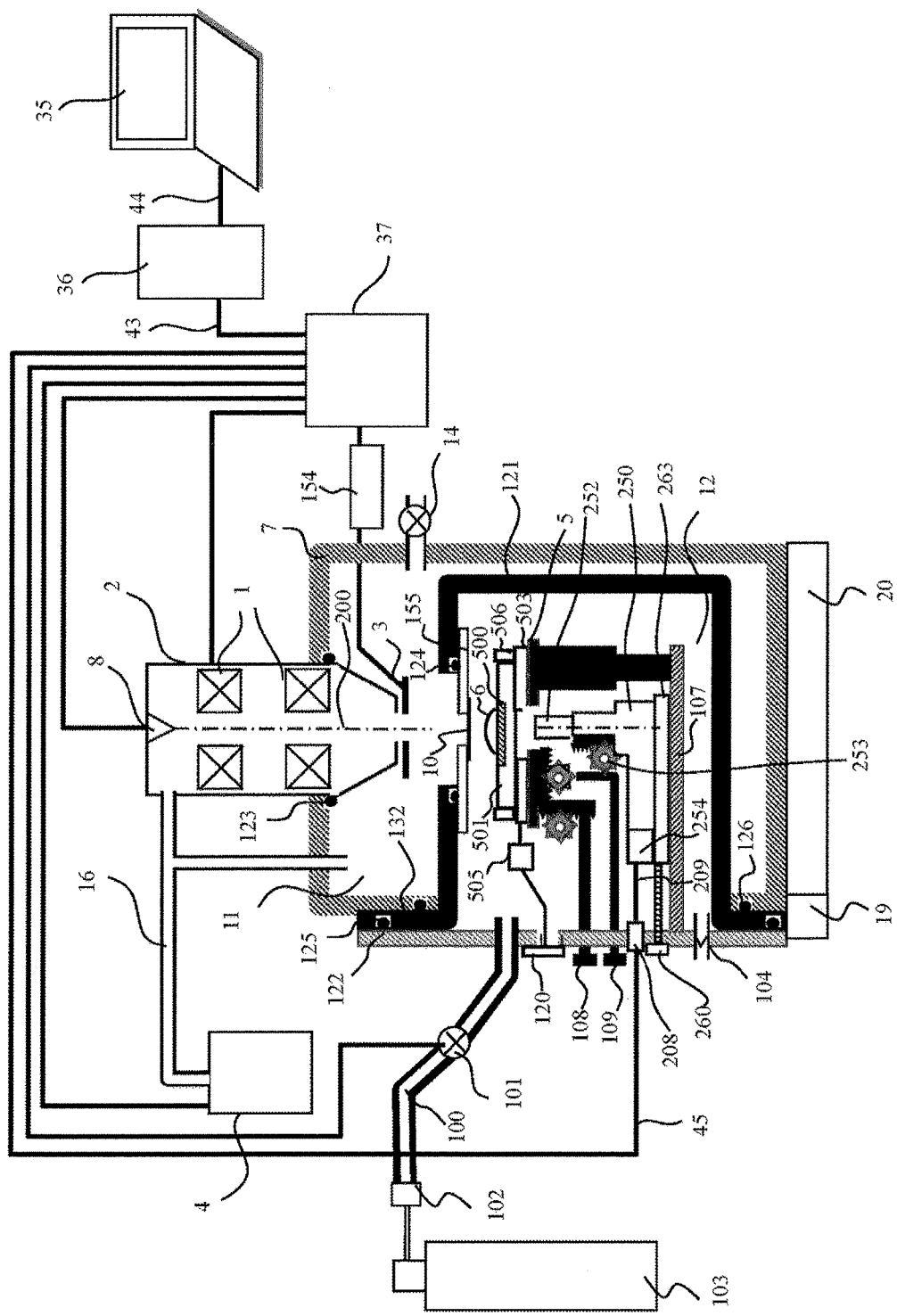

[Fig. 28]
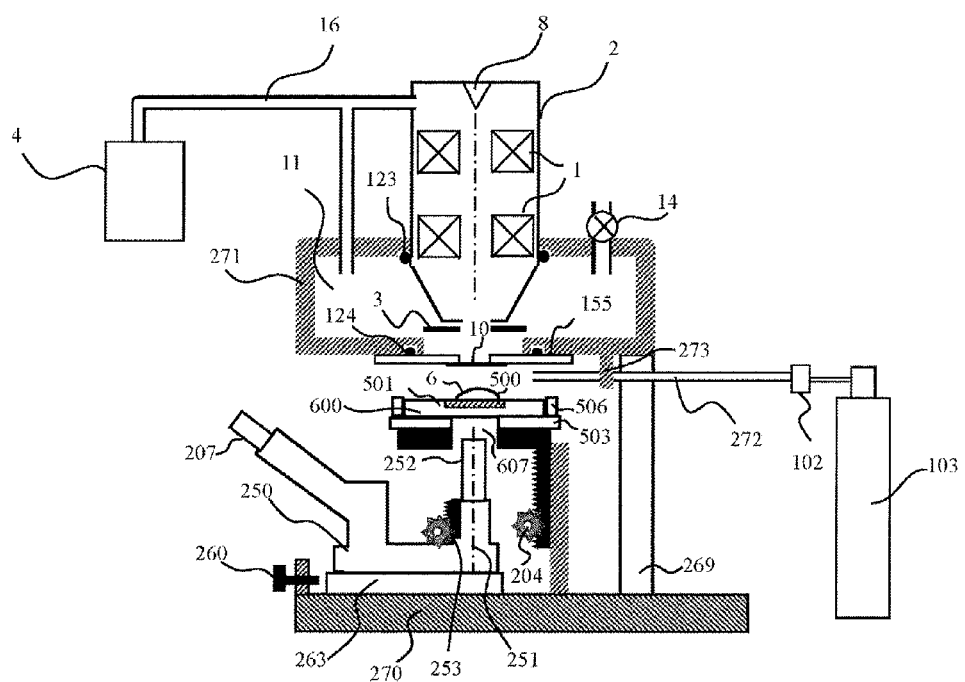

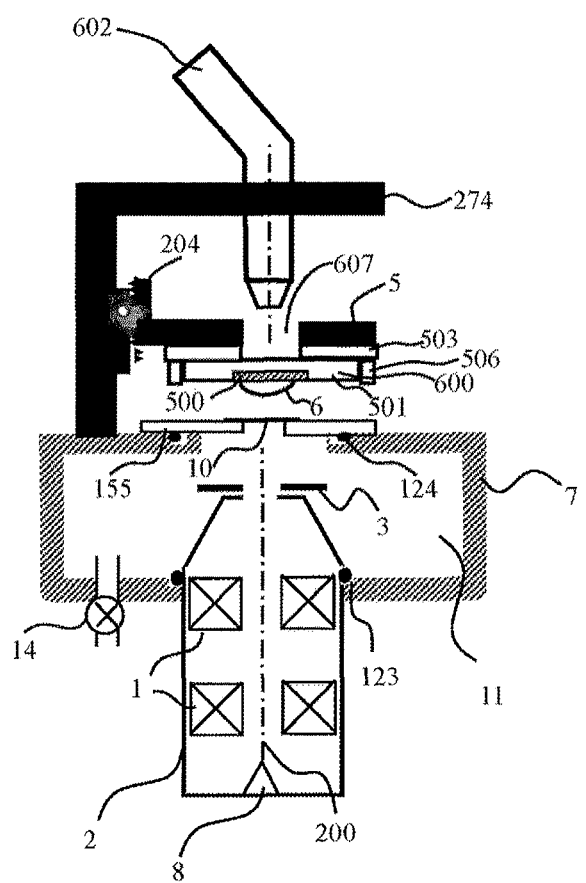
[Fig. 29]

[Fig. 30]
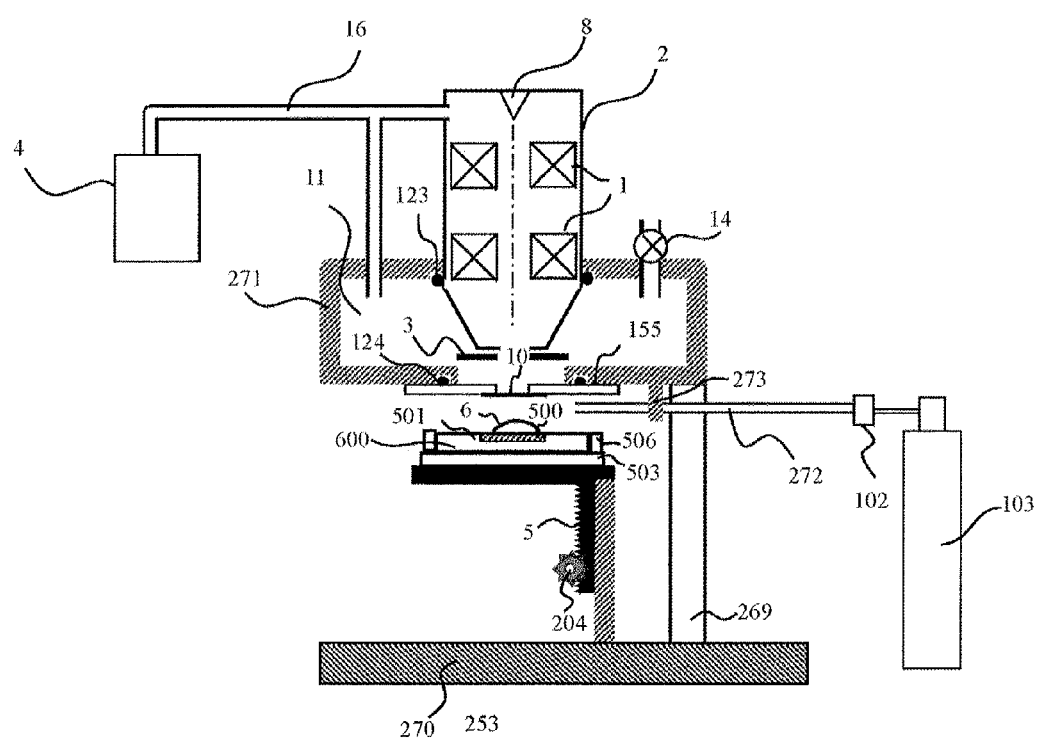

CHARGED PARTICLE BEAM DEVICE, SAMPLE OBSERVATION METHOD, SAMPLE PLATFORM, OBSERVATION SYSTEM, AND LIGHT EMITTING MEMBER

TECHNICAL FIELD

The present invention relates to a charged particle beam apparatus that makes it possible to observe the inside of a sample and a sample support thereof.

BACKGROUND ART

In order to observe an inner structure in a minute region of a substance, a scanning transmission electron microscope (STEM), a transmission electron microscope (TEM), or the like is used. As a typical observation method of observing the inside of a sample by using such an electron microscope, a method has been known in which a sample that is sliced into such a thickness that an electron beam can be transmitted therethrough is arranged on a meshed sample support with multiple pores and the transmitted electron beam is obtained by a detector that is arranged on a side opposite to an electron source side with respect to a sample surface. However, since the method employs a configuration in which the sample floats over pores of the mesh, it is significantly difficult to perform an operation of mounting the sample on the sample support. Thus, PTL 1 proposes an electron detector on which a sample to be observed is directly placed.

In addition, a minute region of a substance can also be observed by an optical microscope as well as the electron microscope. By using the optical microscope, it is possible to obtain color information that cannot be obtained by the electron microscope in principle. According to the optical microscope, it is possible to obtain a transmission optical image by irradiating a sample with white light or specific light and forming an image from light which is absorbed by or emitted from the sample and has color information. In doing so, it is possible to dye only a specific region in a sample, such as biological cells, by applying a specific coloring material to the cells and to thereby observe which region has been dyed or has not been dyed by observing the color. This method has been widely used in the fields of pathologic diagnosis and life sciences, in particular.

While the electron microscope cannot obtain color information, the electron microscope can observe a minute region, which cannot be observed by the optical microscope, with high resolution. In addition, information that can be obtained from an image of the electron microscope is information reflecting differences in density of the sample and is different from information that can be obtained by the optical microscope.

CITATION LIST

Patent Literature

PTL 1: JP-A-10-283978

SUMMARY OF INVENTION

Technical Problem

According to a sample support that also functions as a detector as disclosed in PTL 1, a sample is arranged directly on an electrical system wired to a semiconductor, a metal film, or the like with electric wiring or the like. Since the wiring is connected to the sample support that also functions as a detector, significant time and effort are required to disconnect the electric wiring in order to observe the same sample with another apparatus. In a case of observing cultured cells which require culturing of the sample itself on the sample support for observation with the microscope, for example, a circuit with the electric wiring connected thereto is dipped into a culture solution or the like, and it becomes difficult to place the circuit on the sample that also functions as a detector, in some cases. As described above, installation and extraction of a sample for observation by the transmission charged particle requires significant time and effort in the related art.

The present invention was made in view of such problems, and an object thereof is to provide a charged particle beam apparatus, a sample observation method, a sample support, an observation system, and a light-emitting member that make it possible to simply observe an image by a transmission charged particle.

Solution to Problem

In order to solve the aforementioned problem, the present invention is configured to generate a transmission charged particle image of a sample by detecting light that is caused by charged particles which have been transmitted through or scattered in the sample being incident on a light-emitting member on which the sample as a target of the irradiation of a charged particle beam is arranged directly or via a predetermined member.

Advantageous Effects of Invention

According to the present invention, it is possible to simply observe an image by a transmission charged particle by causing a sample support with a sample placed thereon to emit light and detecting the emitted light.

Problems, configurations, and advantages other than those described above will be clarified by the following descriptions of the embodiments.

BRIEF DESCRIPTION OF DRAWINGS

FIG. 1 is an outline exemplary diagram of observation with an optical microscope and observation with a charged particle beam microscope.

FIG. 2 is a detailed diagram of a sample support that is provided with a detection element.

FIG. 3 is

FIGS. 10A-10D are an explanatory diagram for observing cultured cells.

FIG. 11 is a detailed diagram of the sample support that is provided with the detection element.

FIGS. 12A and 12B are a detailed diagram of the sample support that is provided with the detection element.

FIG. 13 is an explanatory diagram for detecting a transmission charged particle from the detection element.

FIG. 14 is an explanatory diagram for detecting the transmission charged particle from the detection element.

FIG. 15 is an explanatory diagram of a light-emitting region in a detection element according to a first embodiment.

FIG. 16 is an explanatory diagram of an observation method according to the first embodiment.

FIG. 17 is an overall configuration diagram for performing observation with the charged particle microscope according to the first embodiment.

FIG. 18 is an overall configuration diagram for performing observation with the charged particle microscope according to the first embodiment.

FIG. 19 is a configuration diagram for performing observation with the optical microscope according to the first embodiment.

FIG. 20 is an explanatory diagram of a light-emitting region in a detection element according to a second embodiment.

FIG. 21 is an overall configuration diagram for performing observation with a charged particle microscope according to the second embodiment.

FIG. 23 is an overall configuration diagram for performing observation with the charged particle microscope according to the second embodiment.

FIG. 24 is a configuration diagram of a composite apparatus of a charged particle beam microscope and an optical microscope according to a third embodiment.

FIG. 26 is a configuration diagram of the composite apparatus of the charged particle beam microscope and the optical microscope according to the third embodiment.

FIG. 27 is a configuration diagram of a composite apparatus of a charged particle beam microscope and an optical microscope according to a fourth embodiment.

FIG. 28 is a configuration diagram of a composite apparatus of a charged particle beam microscope and an optical microscope according to a fifth embodiment.

FIG. 29 is a configuration diagram of a composite apparatus of a charged particle beam microscope and an optical microscope according to a sixth embodiment.

FIG. 30 is a configuration diagram of a charged particle beam microscope according to a seventh embodiment.

DESCRIPTION OF EMBODIMENTS

Figure 3A:
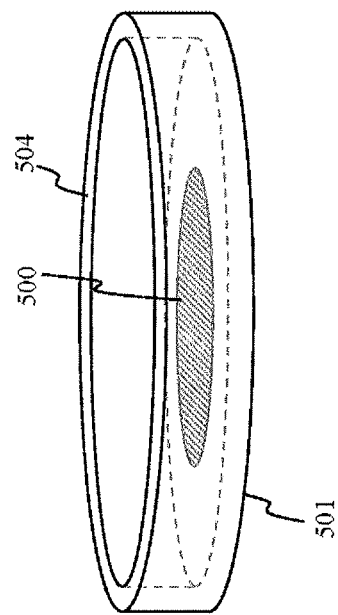
FIGS. 3A and 3B are a detailed diagram of the sample support that is provided with the detection element.

Hereinafter, the respective embodiments will be described with reference to drawings.

A detailed description of a sample support according to the present invention and a description of a charged particle beam apparatus to which the sample support is applied will be given below. However, this is only an example of the present invention, and the present invention is not limited to the embodiment described below. The present invention can be applied to an apparatus for observing a sample by irradiation with a charged particle beam, such as a scanning electron microscope, a scanning ion microscope, or a scanning transmission electron microscope, a composite apparatus of such an apparatus and a sample processing apparatus, and an analysis and inspection apparatus as an application thereof. The sample support according to the present invention and the charged particle beam apparatus on which the sample support is placed configure an observation system that makes it possible to observe a transmission charged particle beam image.

In the specification, "atmospheric pressure" is an air atmosphere or a predetermined gas atmosphere and means a pressure environment at atmospheric pressure or a slightly negative pressure. Specifically, the atmospheric pressure ranges from about $10^5$ Pa (atmospheric pressure) to about $10^3$ Pa.

In the specification, a "sample support" means a unit that can be detached from the charged particle beam apparatus along with a sample in a state in which the sample is placed thereon. Specifically, the "sample support" unit may include a light-emitting member and a base or may be formed only of the light-emitting member as will be described later.

First Embodiment

Outline

First, a description will be given of an outline of the embodiment. In the embodiment, a charged particle microscope and an observation system that generate a transmission charged particle beam image by transforming a charged particle beam transmitted through or scattered in a sample into light and detecting the light will be described. More specifically, at least a part of a sample support on which a sample is placed is formed of a light-emitting member that emits light in response to irradiation with a charged particle beam, light is generated by irradiation of the light-emitting member with the charged particle beam that is transmitted through or is scattered in the sample placed on the light-emitting member, and a transmission charged particle beam image is generated by detecting the light with a detector provided in the charged particle microscope. That is, in the embodiment, the charged particle beam that is transmitted through the sample is not directly detected but is transformed into light and the light is then detected. As will be described in detail later, the light-emitting member that transforms the charged particle beam into light does not require wiring, such as a power cable and a signal line, connected from the outside. For this reason, it is possible to observe a sample with the charged particle beam microscope and another apparatus by using the same sample support, and significant time and effort are not required for disconnecting the electric wiring when the sample is moved between the apparatuses. In addition, it is possible to simply attach and detach the light-emitting member itself or the sample support including the light-emitting member to and from the apparatuses and to thereby easily set any sample on the sample support. This is significantly effective in a case of observing cultured cells, which require culturing the sample itself on the sample support for observation with the microscope, in particular.

Furthermore, it is possible to perform observation with the charged particle beam microscope and observation with another apparatus such as an optical microscope if the sample support according to the embodiment is used as illustrated in FIG. 1. FIG. 1 illustrates a sample support 600 according to the embodiment that is provided with a detection element 500 (also referred to as a light-emitting member) capable of emitting light by transforming or amplifying the charged particle beam into light, a charged particle beam microscope 601, and an optical microscope 602. A sample 6 can be mounted to the sample support 600.

In the embodiment, the detection element that is provided with the sample support is preferably made of a transparent member. Hereinafter, "transparent" in the specification means that visible light, ultraviolet light, or infrared light in a specific wavelength region can be transmitted, or that visible light, ultraviolet light, or infrared light in the entire wavelength region can be transmitted. The ultraviolet light is light in a wavelength region from about 10 nm to about 400 nm, the visible light is light in a wavelength region from about 380 nm to about 750 nm, and the infrared light is light in a wavelength region from about 700 nm to about 1 mm (=1000 μm). For example, it is considered that visible light in the specific wavelength region can be transmitted in a case of a see-through material even if a color is slightly mixed, and that visible light in the entire wavelength region can be transmitted in a case of a colorless transparent material. Here, "can be transmitted" means that a sufficient amount of light for observation with the optical microscope is transmitted by at least the light in the wavelength region (the transmittance is preferably equal to or greater than 50%, for example). In addition, the specific wavelength region described herein is a wavelength region including at least a wavelength region that is used for the observation with the optical microscope. Therefore, it is possible to use the wavelength region for a typical optical microscope (transmission optical microscope) that is capable of detecting a "light transmission signal", which is obtained in response to light being transmitted through a sample from one surface side of the sample support according to the embodiment, from the other surface side of the sample support. Any optical microscope can be employed as long as the microscope employs light, such as a biological microscope, a stereoscopic microscope, an inverted microscope, a metallurgical microscope, a fluorescence microscope, or a laser microscope. Although a "microscope" is exemplified for illustrative purposes, the present invention is generally applicable to apparatuses that obtain information by irradiating a sample with light regardless of a magnifying power of an image.

According to the embodiment, it is possible to obtain a transmission charged particle microscope image by irradiating the sample 6 with a charged particle beam that is generated in the charged particle beam microscope and then detecting a "charged particle transmission signal" that is transmitted through or scattered in the sample by a detection element that is provided in the sample support. As will be described later, an optical detector 503 is provided in the charged particle beam microscope 601 in order to transform or amplify the light from the detection element 500 into an electrical signal.

Since information obtained by an electron microscope and information obtained by an optical microscope are different, there have been more requirements for observing the same sample by both the electron microscope and the optical microscope. However, light cannot be transmitted through the sample support that also functions as a detector as disclosed in PTL 1, for example, and the sample support is for the electron microscope and does not allow observation by the optical microscope in practice. For this reason, it is necessary to separately produce a sample for the electron microscope and a sample for the optical microscope, and there is a problem in that creation of the samples requires time and effort.

Since the sample support according to the embodiment can be mounted to a charged particle beam microscope apparatus such as an electron microscope, the sample support can be a common sample support that can be commonly used for both the electron microscope and the optical microscope. That is, it is possible to perform charged particle beam observation and optical observation while a sample is arranged on one sample support by moving the same sample supports between the respective microscopes as illustrated by the arrow in the drawing and observing the sample without producing a plurality of samples for the observation with both the microscopes or moving the sample therebetween. In addition, the same sample support may be mounted to the respective microscopes that are individually arranged as illustrated in FIG. 1, or a composite microscope apparatus in which an optical microscope and a charged particle microscope are integrated may be used as will be described later. Hereinafter, a detailed description will be given of the sample support, a sample installation method, an image acquisition principle, an apparatus configuration, and the like.

<Description of Sample Support>

A detailed description will be given of the sample support according to the embodiment with reference to FIG. 2. The sample support according to the embodiment is configured of the detection element 500 that transforms a charged particle beam into light and a base 501 (also referred to as a transparent member when the base 501 is transparent) that supports the detection element 500. When observation with the optical microscope and observation with the charged particle microscope are performed by using the same sample support, it is preferable that the detection element 500 and the base 501 are transparent. The sample 6 is mounted directly on the detection element 500. Alternatively, the sample 6 may be mounted indirectly via a member such as a film as will be described later. Although the base 501 is ideally colorless and transparent, a slight color may be mixed. As the base 501, a transparent glass, a transparent plastic, a transparent crystal substance, or the like is used. In a case in which it is desired to perform observation with a fluorescence microscope or the like, plastic is preferably used since it is better that fluorescent light is not absorbed. According to the sample support of the embodiment, it is possible to perform optical observation with a microscope as long as at least the detection element and the base 501 that are between a location where the sample is arranged and a surface that faces the location, at which the sample is arranged, on the sample support are "transparent". Moreover, the base 501 is not necessarily provided as will be described later.

The detection element 500 is an element that detects a charged particle beam that flies with energy from about several keV to about several tens of keV, for example, and emits light, such as visible light, ultraviolet light, or infrared light, when being irradiated with the charged particle beam. In a case of being used in the sample support according to the embodiment, the detection element transforms a charged particle, which is transmitted through or scattered in the sample placed on the sample support, into light. As the detection element, a scintillator, a luminescent light-emitting material, a YGA (yttrium, aluminum, garnet) element, a YAP (yttrium, aluminum, perovskite) element, and the like are exemplified. As the light-emitting wavelength, a specific or arbitrary wavelength region among those of visible light, ultraviolet light, and infrared light may be used. Examples of the scintillator include an inorganic scintillator made of an inorganic material such as SiN, a plastic scintillator or an organic scintillator that is contained in a material capable of emitting light such as polyethylene terephthalate, and a material coated with a liquid scintillator contained in anthracene or the like. The detection element 500 may be made of any material as long as the element can transfer the charged particle beam into light. In addition, the detection element is not limited to an attachable and detachable solid, and may be a thin film or a fine particle coated with a fluorescent agent that emits fluorescent light in response to irradiation with the charged particle beam. In the embodiment, members that emit light in response to reception of the charged particles by light-receiving surfaces, which include the aforementioned examples, will be collectively referred to as light-emitting members. A mean free path in solid of the charged particle beam depends on an acceleration voltage of the charged particle beam and ranges from several tens of nm to several tens of μm. Therefore, the light-emitting region in the upper surface of the detection element 500 is a region with the same thickness from the surface of the detection element. Accordingly, it is only necessary that the thickness of the detection element 500 exceeds the thickness. In contrast, in a case in which performing observation with the optical microscope using the same sample support is taken into consideration, it is necessary that the light transmission signal during the observation with the optical microscope can be transmitted as much as possible. Therefore, it is preferable that the thickness of the detection element is as thin as possible if a slight color is mixed therein.

In addition, the detection element 500 may be a thin film or a fine particle coated with a fluorescent agent that emits fluorescent light in response to irradiation with the charged particle beam. As a fabrication method, it is possible to employ a method of dissolving the fluorescent agent in a solvent such as water or alcohol and spin-coating or dip-coating a prepared slide with the mixture. Alternatively, the mixture may be sprayed to coat the prepared slide.

Figure 3B:
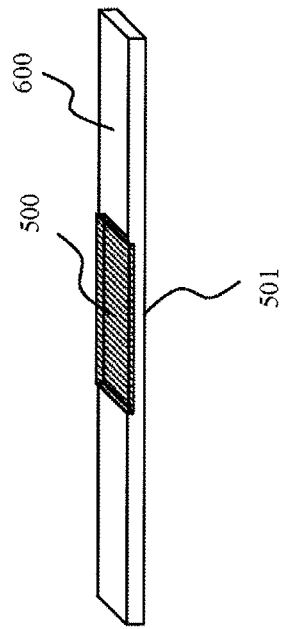

As sample supports that are used often with the optical microscope, there are transparent sample supports such as a slide glass (or a prepared slide) and a dish (or a petri dish). That is, if a sample support provided with the detection element, which is capable of transforming the charged particle beam into light, according to the embodiment is formed into a shape of a typical slide glass (for example, about 25 mm×about 75 mm×about 1.2 mm) dedicated for the optical microscope, it is possible to mount and observe a sample in the same manner as that in which a user previously experienced or felt during usage. Therefore, it is possible to use the sample support for primary screening with the optical microscope and for detailed observation of a selected sample with the charged particle microscope. Alternatively, it is possible to perform observation by using the sample support according to the embodiment as screening prior to observation with a high-performance transmission charged particle beam microscope since preparation of a sample by a typical high-performance transmission charged particle beam microscope device requires significant effort. In addition, a slide glass case and a sample mounting device for the optical microscope, which are owned by a user of the optical microscope, can be utilized. Although FIG. 2 illustrates a sectional shape of a slide glass, a dish (or petri dish) shape as illustrated in FIG. 3 may be employed. FIG. 3(*a*) is a sectional view, and FIG. 3(*b*) is an arrow view. Since a side wall 504 is provided at a circumferential edge at a portion where a sample is to be arranged as compared with FIG. 2, the sample such as liquid does not leak.

Figure 4A:
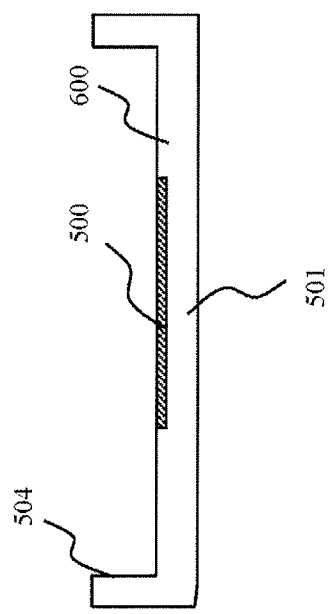
FIGS. 4A and 4B are a detailed diagram of the sample support that is provided with the detection element.
Figure 4B:
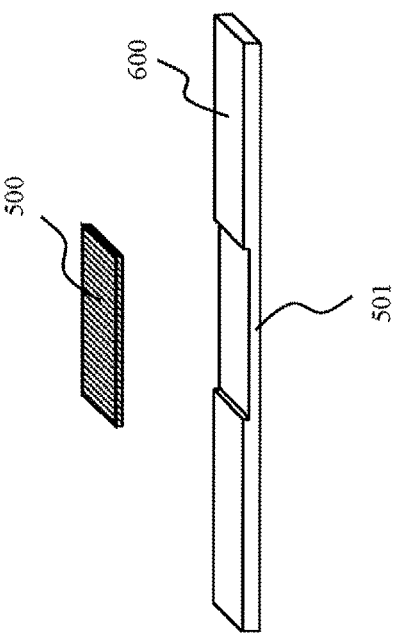

FIGS. 2 and 3 illustrate a state where the position of the upper surface of the detection element 500 coincides with the position of the upper surface of the base 501. In order to make it possible to cause the user of the optical microscope to mount the sample in the same manner as that in which the user previously felt and experienced when using a slide glass or a petri dish, it is desirable that the upper surface (that is, the location on which the sample is arranged) of the detection element 500 is made to coincide with the upper surface of the base 501 at the same height such that not much unevenness is present between the detection element 500 and the base 501. FIG. 4 illustrates an example of the sample support in which the upper surface of the detection element 500 coincides with the upper surface of the base 501. As a fabrication method, it is only necessary to separately produce the detection element 500 and the base 501, providing a concave portion to a transparent member, such as glass or plastic, for the base 501, and fitting the detection element 500 thereinto. If one of the detection element 500 and the base 501 projects from the other, optical plane grinding by polishing or the like may be performed. The base 501 and the detection element 500 are fixed to each other with an adhesive, a double-stick tape, a mechanical fitting, or the like. Alternatively, the base 501 and the detection element 500 may be bonded to each other by chemical bonding. Alternatively, optical grinding may be performed until the detection element is exposed to the surface of the sample support after producing the detection element 500 and the base 501 while fitting the detection element 500 thereinto from the beginning.

Figure 5A:
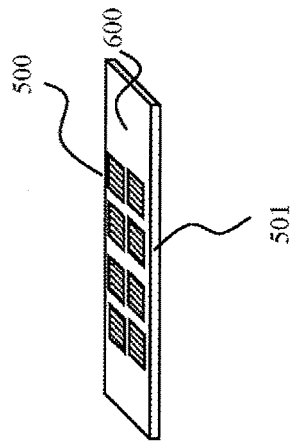
FIGS. 5A and 5B are a detailed diagram of the sample support that is provided with the detection element.
Figure 5B:
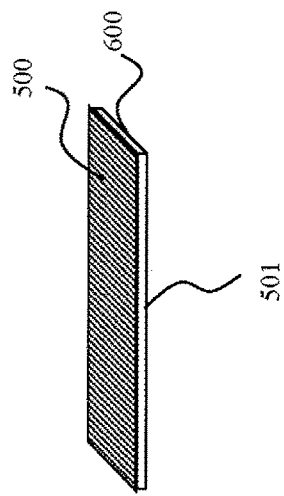

If it is possible to use a significantly large detection element, the entire surface of the sample support may be configured as the detection element as illustrated in FIG. 5(*a*). That is, the detection element itself may be used as the sample support, or alternatively, the entire region on the side of the surface, on which the sample is placed, of the transparent member may be used as the light-emitting member. In such a case, it is possible to obtain a transmission signal of the charged particle beam at any positions on the sample support. According to another configuration, a plurality of detection elements may be arranged on a transparent member as illustrated in FIG. 5(*b*). In a case in which there are a plurality of samples, this configuration makes it possible to easily recognize which sample is present at which detection element position.

Figure 6A:
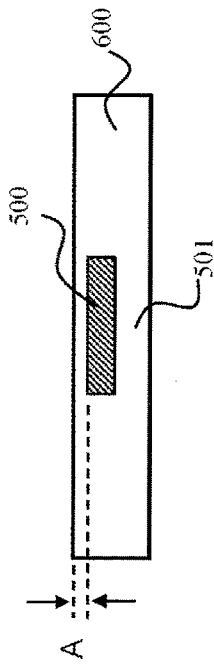
FIGS. 6A and 6B are a detailed diagram of the sample support that is provided with the detection element.
Figure 6B:
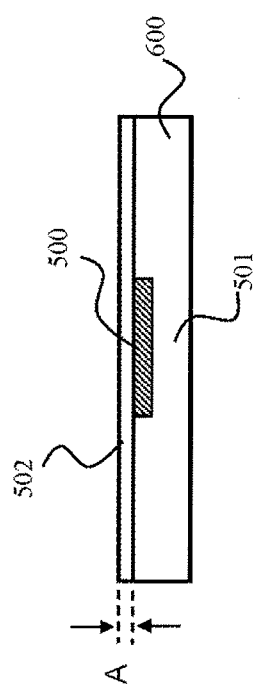

Since the mean free path in solid of the charged particle beam ranges from several tens of nm to several tens of μm while depending on the acceleration voltage of the charged particle beam as described above, a film 502 that is sufficiently thinner than the mean free path may be arranged between the detection element 500 and the sample. That is, the sample is placed on the thin film 502 that covers the detection element 500. The sample support will be shown in FIG. 6(*a*). The thickness is illustrated as A in the drawing. It is necessary that the thin film 502 is transparent with respect to the charged particle beam. That is, it is necessary to select a thickness and a material that allow at least a part of the charged particle beam to be transmitted. In a case of the observation with the optical microscope, it is further necessary that the thin film 502 is transparent to light. By arranging such a thin film 502, it is possible to prevent the surface of the detection element 500 from being contaminated or scratched, for example. However, if the thin film 502 is an insulating substance, there is a possibility of electrification during irradiation of the detection element 500 with the charged particle beam in vacuum and it becomes difficult to observe the sample. Therefore, the thin film 502 in FIG. 6(a) is made of a conductive member such that it is possible to remove the electrification. In addition, the thin film 502 and the base 501 may be integrally formed into a same member as illustrated in FIG. 6(b). That is, it is possible to produce the sample support in FIG. 6(b) by producing the base 501 and the detection element 500 while fitting the detection element 500 into the base 501 and performing optical grinding until the distance between the upper surface of the detection element 500 and the base 501 becomes A. This results in prevention of the surface of the detection element 500 from being contaminated or scratched, for example, at low cost since less types of members are used as compared with the sample support in FIG. 6(a). Although not shown in the drawing, the portion represented as A in the drawing may include an uneven shape, for example. In such a case, it is possible to arrange a space of a predetermined distance, namely a gas material of a predetermined type and pressure between the mounted sample and the detection element 500. As described above, a predetermined member in the form of solid, liquid, or gas may be arranged between the light-emitting member and the sample, and the sample may be arranged on the light-emitting member via the predetermined member.

In a case of using a slide glass (or a prepared slide) or a dish (or a petri dish) that is used often with the optical microscope, the sample support is coated with a material for enhancing adhesiveness between the sample and the sample support in order for the sample not to be separate from the sample support in some cases. In a case in which the sample is a biological sample such as cells, for example, the surface of the cells is in a negatively charged state due to a phospholipid bilayer. Therefore, peeling-off of the cell sample from the sample support is prevented by coating the sample support such as a slide glass with a molecule (lysine, aminosilane, or the like) in a positively charged state in some cases. For this reason, the molecule in the positively charged state may adhere to the sample support 600 or the detection element 500 in the same manner. Alternatively, coating with a material with hydrophilicity may be performed in order to facilitate the mounting of the sample that contains a large amount of liquid. Alternatively, coating with a material with high affinity with a biological sample such as collagen may be performed in order to facilitate mounting or cultivation of living cells or bacteria. Coating described herein widely includes methods of causing a coating material to adhere to the surface of the sample support, such as spraying, dipping, and coating. In addition, the molecule or the film may be arranged only at a predetermined position. The predetermined position described herein means a partial region in the detection element 500. In a case in which the molecule in the positively charged state is arranged only at the predetermined position, for example, it is possible to arrange the sample only at the predetermined position in a case in which the sample is a biological sample such as cells. This method is effective when it is desired to shorten the observation time by narrowing a region as a target of observation. In addition, a conductive member (electrification prevention member) may be provided at least on the surface on which the sample is placed in order not to cause electrification during irradiation with the charged particle beam. Examples of the conductive member include a carbon material, a metal material, and a conductive organic substance. Such a molecule, a coating material, an electrification preventing film, and the like are arranged at the position represented as A in FIG. 6(a).

Figure 7A:
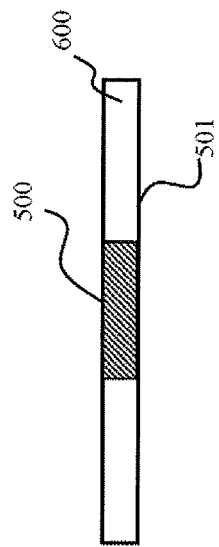
FIGS. 7A and 7B are a detailed diagram of the sample support that is provided with the detection element.
Figure 7B:
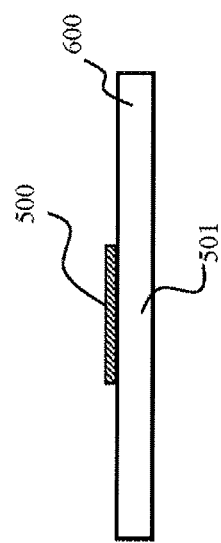

The detection element 500 may slightly project from the surface of the sample support 600 as illustrated in FIG. 7(a) as long as it is possible to mount the sample in the same manner as that in which the user previously experienced and felt. For example, the fabrication can be made by a method of attaching the detection element 500 with a thickness of several hundreds of μm or less to the base 501. In such a case, since the base 501 has a significantly simple shape and the area of the detection element 500 is small, it is possible to produce the sample support at low cost. In addition, the thickness of the transparent member may be the same as that of the detection element, and such a shape that a portion from the upper surface to the lower surface of the sample support is made to function as the detection element 500 may be employed as illustrated in FIG. 7(b) as long as it is possible to produce or obtain the detection element 500 itself at low cost. In such a case, the base 501 functions as a base for supporting the detection element 500.

Figure 8A:
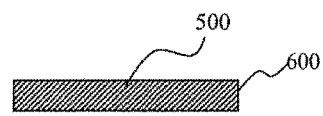
FIGS. 8A-8C are a detailed diagram of the sample support that is provided with the detection element.
Figure 8B:
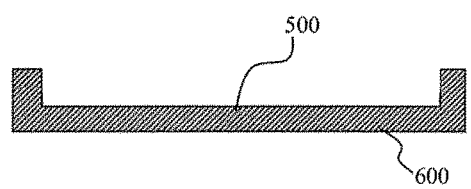
Figure 8C:
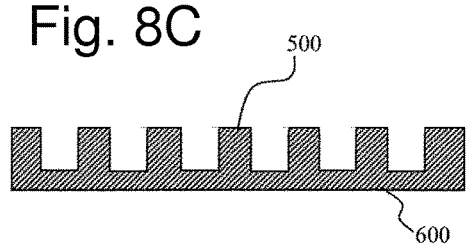
Figure 9A:
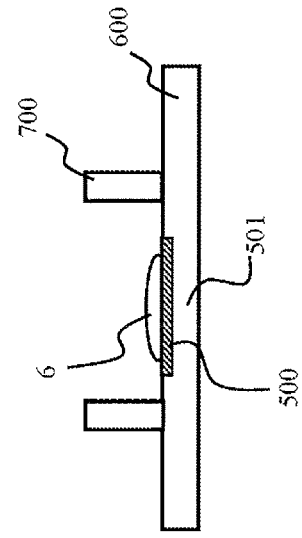
FIGS. 9A-9D are a detailed diagram of the sample support that is provided with the detection element.
Figure 9B:
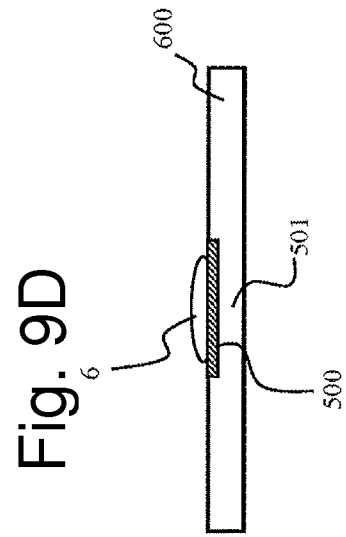
Figure 9C:
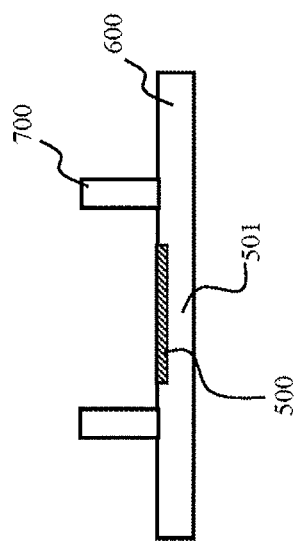
Figure 9D:
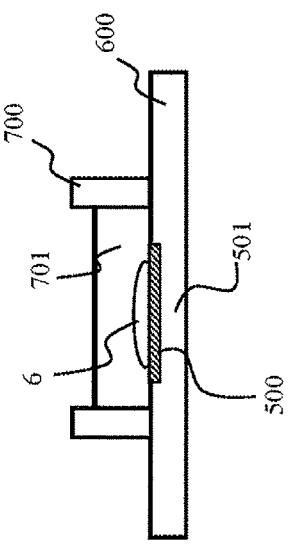

The entire sample support 600 may be made to function as the detection element 500 as illustrated in FIG. 8 as long as it is possible to produce the detection element 500 at significantly low cost. That is, the base 501 is not provided. FIG. 8(a) illustrates a simple flat sample support such as a slide glass. In contrast, FIGS. 8(b) and 8(c) illustrate examples in which the sample support has concave shapes. The sample is placed in the concaves and does not leak even in a case of a liquid sample. FIG. 8(b) illustrates a sample container configured such that the sample does not leak from side surfaces, such as a petri dish, and FIG. 8(c) illustrates a culture container (a micro plate or a titer plate) with a plurality of places where the sample is stored. The light-emitting member may have anyone of the shapes in FIGS. 8(a), 8(b), and 8(c), or may have a shape other than the shapes illustrated in the drawings. In this case, there is an advantage in that production cost is not required since only one type of material is used.

If it is necessary that the detection element 500 has the same size as that of a slide glass with which the user is familiar, it is also possible to just attach the detection element 500 to the slide glass as illustrated in FIG. 7(a). By producing the detection element 500 to have the same size as that of the slide glass, enhanced convenience is achieved in a case in which the detection element 500 is stored in a case for the slide glass, in a case in which the detection element 500 is mounted to a sample holder for the slide glass, and in a case in which the detection element 500 is mounted to a sample stage with a size of the slide glass of the optical microscope, for example. In a case in which the detection element 500 is a plastic scintillator configured of plastic, the sample support in FIG. 8(a) itself can be formed to have the size of the slide glass as long as it is possible to produce the sample support at significantly low cost.

As illustrated in FIG. 9, the sample support according to the embodiment can be integrated with a culture container. This example is preferable because in a case in which the sample is a biological sample, it is possible to culture or cultivate a sample on the light-emitting member and to omit an operation of moving the sample to the sample support. A container 700 is arranged on the sample support 600 (FIG. 9(a)). The container 700 is a cylindrical tubular member with opened surfaces on upper and lower sides, for example. Next, the sample 6 such as cells and a culture medium 701 that contains a nutritional material capable of providing nutrition and energy to the sample, such as a culture solution, are mounted on the inside of the container 700 (FIG. 9(b)). The form of the culture medium. 701 may be any one of solid, liquid, and gas. In addition, a leakage prevention member such as a rubber or a packing may be provided in order not to cause the culture medium 701 to leak from a space between the sample support 600 and the container 700. Thereafter, the sample is cultured, and the culture medium 701 such as a culture solution is then removed (FIG. 9(c)). Then, it is possible to obtain a state in which the sample 6 adheres to the detection element 500 by peeling off the container 700 from the sample support 600 (FIG. 9(d)). Although only one detection element 500 and only one container 700 are illustrated in the drawings, a plurality of detection elements 500 and a plurality of containers 700 may be arranged on a single sample support. In addition, it is necessary that the sample is thin since the charged particle beam (and light in a case of the transmission optical observation) is required to be transmitted therethrough. For example, the thickness is from about several tens of nm to about several tens of μm. Therefore, it is necessary that the aforementioned cultured cells have substantially the same thickness as that described above after the culture. Examples of the cultured cells include cultured nerve cells, blood cells, and iPS cells. Alternatively, the cultured cells may be bacteria or viruses. By using the method, it is possible to obtain a transmission charged particle microscope image and an optical microscope image while the cell sample cultured on the sample support 600 remains mounted on the sample support 600.

Alternatively, it is only necessary to place the detection element 500 on an existing culture container as illustrated in FIG. 10(a). An example in which a sample is arranged by the method will be shown in FIG. 10(b). Here, an exemplary procedure for culturing a cultured cell on the detection element 500 and observing the cultured cell with a charged particle microscope apparatus and an optical microscope apparatus will be described. First, the light-emitting member 500 with a desired size is placed in advance in a culture container 808 as illustrated in FIG. 10(a). Then, a culture solution 806, a sample 807, and the like are injected as illustrated in FIG. 10(b), and culture and the like is made to proceed. Next, the detection element 500 is extracted while the sample 807 is mounted thereon as illustrated in FIG. 10(c). Then, observation with the optical microscope 602 and the charged particle microscope 601 can be performed by extracting the detection element 500 as necessary as illustrated in FIG. 10(d) after performing desired pre-processing such as fixing, drying processing, metal dyeing, or immunostaining. In addition, the observation can be performed without any additional operation in the case of the observation with the optical microscope, or the observation may be performed after arranging the detection element 500 on a transparent member such as a slide glass. In addition, a culture container (a micro plate or a titer plate) that is capable of performing a plurality of culture operations as illustrated in FIG. 11 may be used as the culture container. In such a case, it is possible to prepare a plurality of samples at the same time by placing a plurality of detection elements 500 in advance. If the detection element 500 as the light-emitting member is an inexpensive detection element with high workability, such as a plastic scintillator, as described above, the culture container 808 itself may be used as the detection element 500.

The sample support 600 can be used not only with the charged particle beam microscope but also with the optical microscope, and it is also possible to observe the sample on the sample support with an inverted optical microscope in which a field lens 251 is arranged on the opposite side to the surface to which the sample is mounted as will be described later. In such a case, there is a case in which it is desired to cause the field lens 251 of the optical microscope to approach the sample as much as possible. If the distance between the field lens 251 and the sample 6 is represented as L, there is a case in which it is desired to set L to be equal to or less than about several hundreds of μm.

Although a method is considered in which the entire sample support 600 provided with the detection element 500 is formed to have a thin thickness of equal to or less than the distance L, there is a case in which intensity is low since the sample support 600 itself is excessively thin. Thus, it is also possible to form a transparent member at a portion, on which the sample is placed, of the sample support to be thinner than the other portions. That is, it is possible to set the distance between the sample 6 and the field lens 251 to be L by producing regions with thinner thickness at the portion at which the sample is arranged and at the detection element 500 as compared with the thickness of the sample support 600 (B in the drawing) as illustrated in FIG. 12(a). In doing so, it is possible to keep the strength of the sample support 600 itself high since both ends of the sample support are thick. The thick regions on both ends may be arranged on the opposite side as illustrated in FIG. 12(b) or the thick regions may be provided on both upper and lower sides of the sample placement surface as long as the user can mount the sample in the same manner as that in which the user previously experienced or felt.

In addition, a paper or a seal portion on which information related to the sample 6, such as characters, numbers, barcodes, pictures, and the like can be written may be provided on the sample support 600. In such a case, it becomes easier to manage the sample 6 that is mounted to the sample support.

Although not shown in the drawing, ion liquid may be arranged above, inside, or around the sample to be observed. The ion liquid has a characteristic that it is possible to apply conductivity to an electron irradiation surface. By arranging the ion liquid inside or around the sample to be observed, it is possible to prevent electrification of the sample during irradiation with the charged particle beam in vacuum. Furthermore, it is possible to maintain the sample in a wet state by causing the sample to contain the ion liquid. Therefore, it is possible to obtain a transmission image of the wet sample by detecting light emitted by the charged particle beam that has been transmitted through or scattered in the wet sample containing the ion liquid. As a method of mounting the ion liquid to the sample, the sample may be dipped in the ion liquid, or the ion liquid may be sprayed to the sample.

Although not shown in the drawing, if contamination, scratch, or the like is present before usage of the detection element 500, a flat surface may be obtained by cleaning the detection element 500 with an organic solvent or the like in advance, polishing the detection element 500 by using a mechanical or chemical polishing agent, or sputtering the detection element 500 by an ion beam or the like. In addition, a member, through which the charged particle beam can be transmitted, which is as transparent as possible with respect to the light from the light source of the optical microscope and the light emitted by the detection element 500 may be arranged or applied in order not to cause the scratch and the contamination to appear outstandingly.

<Description of Method and Principle>

Hereinafter, descriptions will be given of a light detection method using the sample support according to the embodiment and a principle in which the transmission charged particle beam can be obtained. FIG. 13 illustrates a state in which the sample 6 is arranged on the detection element 500. A light detector 503 is illustrated below the sample support. The light detector 503 can transform or amplify the light signal from the detection element 500 into an electrical signal. The transformed or amplified electrical signal is input to a control unit or a computer via a communication line, and such a control system forms an image therefrom. The obtained image (transmission charged particle beam image) may be displayed on a monitor or the like.

Here a case will be considered in which a site 508 with high density and a site 509 with low density are present in a sample. If the site 508 with high density in the sample is irradiated with the primary charged particle beam 510, a major part of the charged particle beam is backscattered. Therefore, the charged particle beam does not reach the detection element 500. In contrast, if the site 509 with low density in the sample is irradiated with the primary charged particle beam 511, the charged particle beam can be transmitted up to the detection element 500. As a result, it is possible to detect a difference in density inside the sample (that is, convert the difference into a light signal) by the detection element 500. The transmission level varies depending on acceleration energy of the charged particle beam. Therefore, it is possible to change internal information to be observed and a region thereof by changing the acceleration energy of the charged particle beam.

Although there may be a space between the light detector 503 and the sample support (the portion h in the drawing), it is preferable that the height h thereof is as short as possible in order to most efficiently detect the light. The sample support may be in contact with the light detector 503. In addition, the light may be most efficiently detected by increasing a light-receiving area of the light detector 503. Alternatively, a light-transmission path for efficiently delivering the light to the portion h between the sample support and the light detector 503. As an example, FIG. 14 illustrates an example in which a light transmission path 811 is provided between the detector and the light-emitting member. It is assumed that the sample support 600 is arranged on the sample stage 5. The light transmission path 811 through which the light is delivered to a lower portion of the sample stage is formed of a light reflective material 809 for causing the light to pass without leaking to the outside of the light transmission path 811 and a light reflective material 810 for guiding the light to the light detector 503. A configuration of the light transmission path 811 is not limited to the example.

The light emitted by the detection element 500 passes to reach the lower portion of the sample support 600 in FIG. 14 and is incident on the light transmission path 811. A track of the light that enters the light transmission path is controlled by the light reflective material 809. An advancing direction of the light that has reached the light reflective material 810 is changed to a direction toward the detection element 503 by the light reflective material 810, and the light passes through the light transmission path 811 and is then detected by the detection element 503. The light transmission path 811 may be a solid substance capable of delivering the light or may deliver the light in the air or in vacuum. Examples of the solid material capable of allowing passage of the emitted light in the wavelength region include a transparent or semi-transparent material with respect to the light such as quartz, glass, optical fiber, or plastic. With such a configuration, it is possible to arrange the light detector 503 so as to be separate from the stage and to thereby arrange the wiring and the electric circuit to be connected to the light detector 503 at positions that are separate from the sample support and the sample stage for holding the sample support. Although the light detector 503 is arranged below the sample support 600 in FIGS. 13 and 14, the light detector 503 may be arranged in the lateral direction or above the sample support 600 as will be described later.

Here, a description will be given of a region from which light is emitted by irradiation of the detection element 500 with the charged particle beam that has passed through the sample, with reference to FIG. 15. The sample 6 adheres to or is in contact with a sample adhesion layer 812 on the detection element 500. As described above, the sample adhesion layer is a layer that is configured such that cells or the like can easily adhere thereto, a conductive film layer for removing electrification due to the charged particle beam, or the like. If the width thereof in the thickness direction is assumed to be represented as A, it is necessary that the width A is thin enough to cause the charged particle beam flying with energy from about several keV to about several tens of keV to reach the light-emitting member. This is from about several nm, to about several hundreds of nm, for example. The charged particle beam that has passed through the sample adhesion layer 812 enters the detection element 500 and causes light emission 814. The light-emitting region 813 that emits light depends on the depth of the entrance of the charged particle beam and energy at the time of the entrance and during the entrance. In a case of the charged particle beam with energy from about several keV to about several tens of keV, for example, the light-emitting region 813 ranges from about several tens of nm to about several μm. If the thickness is assumed to be represented as B and the thickness of the detection element 500 is thicker than the width B, a region (C in the drawing) other than the region represented with the width B does not contribute to the light emission. In order to detect the light emission on the lower side in the drawing, it is desirable that the region C that does not contribute to the light emission and the sample support 600 are transparent enough to minimize a loss of the light emission. Although not shown in the drawing, the light from the light-emitting region 813 is scattered in various directions inside the detection element 500. Thus, it is also possible to deliver the whole light to the lower side in the drawing by providing a metal film capable of reflecting the light to the portion A in the drawing or to the side surface side of the detection element 500 to prevent the generated light from escaping to the upper side in the drawing and the side surface side.

A method of mounting the sample to the sample support will be described below. Since it is necessary to transmit the charged particle beam (and light in a case of using the optical microscope observation together), the sample is required to be thin. For example, the thickness is from about several tens of nm to about several tens of μm. Examples of the sample that can be mounted directly on the detection element 500 include liquid or mucosa containing cells, liquid-form biological specimens such as blood or urine, cells split into a piece, particles in a liquid, fine particles such as fungi, mold, and viruses, and a soft material containing fine particles and an organic substance. As a method of mounting the sample, the following methods can be considered as well as the aforementioned culture. For example, there is a method of dispersing the sample in a liquid and causing the liquid to adhere to the detection element. Alternatively, the sample may be split into a piece with a thickness through which the charged particle beam can be transmitted, and the sample split into the piece may be arranged on the detection element. More specifically, the sample may be made to adhere to a tip end of a cotton swab and applying the sample to the detector or dropping the sample with a dropper. In the case of fine particles, the detector may be sprinkled with the fine particle. Coating of the sample may be performed by spraying the sample, a spin coating method of coating the sample support with liquid during high-speed rotation may be used, or a dip coating method of coating the sample support with liquid by dipping the sample support into the liquid and extracting the sample support therefrom may be employed. Any methods may be employed as long as the sample can have a thickness from about several tens of nm to about several tens of μm.

Next, a description will be given of an exemplary procedure before observation with a microscope with reference to FIG. 16. First, the detection element 500 (the light-emitting sample support) to mount a sample thereon is prepared. Next, predetermined members are arranged on the detection element 500 as necessary. Here, the predetermined members mean the substance for enhancing the adhesiveness between the sample and the sample support, the conductive substance, the substance for reflecting light, or some predetermined gas material as described above. If it is not necessary to arrange the predetermined members, it is not necessary to perform this step. Then, the sample is mounted to the detection element 500. Next, the processing proceeds to a step in which the detection element is mounted to and observed on the charged particle microscope or the optical microscope. Step A is a step of performing observation with the charged particle microscope, and Step B is a step of performing observation with the optical microscope. In Step A, the detection element 500 with the sample mounted thereto as described above is arranged in the charged particle microscope apparatus first. Then, the charged particle beam is made to be transmitted through or scattered in the sample by irradiating the sample with the charged particle beam. Then, since the detection element 500 emits light when the charged particles reach the detection element, the light emission is detected by the light emission detector. Next, a lower-order control unit 37 or the like generates a transmission charged particle image of the sample from the signal detected by the detector. After the observation with the charged particle microscope apparatus is completed, the sample is extracted to the outside of the charged particle microscope apparatus. The processing proceeds to Step B of performing observation with the optical microscope as necessary. In Step B of performing observation with the optical microscope, the detection element 500 with the sample mounted thereto is arranged in the optical microscope apparatus first. If it is necessary that the detection element 500 has the shape of the slide glass when the detection element 500 is arranged in the optical microscope apparatus, it is possible to place the detection element 500 on the slide glass as described above. Next, observation with the optical microscope is performed. After the observation is completed, the detection element 500 may be returned to the charged particle microscope apparatus again for further observation. Steps A and B may be replaced with each other, and the observation may be performed at the same time in a case of an apparatus in which the charged particle microscope apparatus and the optical microscope apparatus are integrated, as will be described later.

<Description of Observation with Charged Particle Beam Apparatus in Vacuum>

Here, FIG. 17 illustrates a typical charged particle beam apparatus to which the sample support according to the embodiment is mounted. The charged particle microscope is configured mainly of a charged particle optical column 2, a case body 7 (hereinafter, also referred to as a vacuum chamber) that supports the charged particle optical column relative to an apparatus installation surface, and a control system that controls the charged particle optical column 2 and the case body 7. When the charged particle microscope is used, the inside of the charged particle optical column 2 and the case body 7 are evacuated by a vacuum pump 4. An activation operation and a stop operation of the vacuum pump 4 are also controlled by the control system. Although only one vacuum pump 4 is illustrated in the drawing, two or more vacuum pumps 4 may be provided.

The charged particle optical column 2 is configured of elements such as a charged particle source 8 that generates the primary charged particle beam and an optical lens 1 that focuses the generated charged particle beam, guides the generated charged particle beam to a lower portion of the column, and scans the sample 6 with the primary charged particle beam. The charged particle optical column 2 is installed so as to project toward the inside of the case body 7 and is fixed to the case body 7 via a vacuum sealing member 123. A detector 3 that detects secondary charged particles (secondary electrons, reflected electrons, or the like) that are obtained by irradiation with the primary charged particle beam is arranged at an end of the charged particle optical column 2. The detector 3 may be provided at any locations in the case body 7 instead of the location illustrated in the drawing.

The secondary charged particles such as reflected charged particles or transmission charged particles are released from the inside or the surface of the sample by the charged particle beam that has reached the sample 6. The secondary charged particles are detected by the detector 3. The detector 3 is a detection element that is capable of detecting and amplifying the charged particle beam that flies with energy from several keV to several tens of keV. For example, a semiconductor detector made of a semiconductor material such as silicon or a scintillator that is capable of transforming a charged particle signal into light on or inside a glass surface is employed.

The charged particle microscope according to the embodiment includes, as control systems, a computer 35 that is used by a user of the apparatus, an upper-order control unit 36 that is connected to the computer 35 and performs communication, and a lower-order control unit 37 that controls a vacuum evacuation system, a charged particle optical system, and the like in response to an order that is transmitted from the upper-order control unit 36. The computer 35 is provided with a monitor that displays an apparatus operation screen (GUI) and input means for the operation screen, such as a keyboard and a mouse. The upper-order control unit 36, the lower-order control unit 37, and the computer 35 are respectively connected via communication lines 43 and 44.

The lower-order control unit 37 is a site that transmits and receives control signals to control the vacuum pump 4, the charged particle source 8, the optical lens 1, and the like, further transforms a signal output from the detector 3 into a digital image signal, and transmits the digital image signal to the upper-order control unit 36. In the drawing, the signal output from the detector 3 is connected to the lower-order control unit 37 via an amplifier 53 such as a preamplifier. The amplifier may not be provided if not necessary.

According to the upper-order control unit 36 and the lower-order control unit 37, an analog circuit, a digital circuit, and the like may be present together, or the upper-order control unit 36 and the lower-order control unit 37 may be collectively provided as one control unit. The configuration of the control systems illustrated in FIG. 17 is only an example, and modification examples of the control units, the valve, the vacuum pump, the communication wiring, and the like belong to the scope of the charged particle beam microscope according to the embodiment as long as the control units, the valve, the vacuum pump, the communication wiring, and the like function as intended in the embodiment.

Vacuum piping 16 with one end connected to the vacuum pump 4 is connected to the case body 7 such that the inside thereof can be maintained in a vacuum state. Also, a leak valve 14 for opening the inside of the case body to the atmospheric air is provided such that the inside of the case body 7 can be opened to the atmospheric air when the sample support is introduced into the apparatus. No leak valve 14 may be provided, or two or more leak valves 14 may be provided. In addition, the arrangement location of the leak valve 14 on the case body 7 is not limited to the position illustrated in FIG. 17, and the leak valve 14 may be arranged at another position on the case body 7.

The case body 7 includes an opening portion provided in the side surface thereof, and the inside of the apparatus is maintained in an air tight vacuum state by a cover member 122 and a vacuum sealing member 124 for the opening portion. The charged particle microscope according to the embodiment is provided with the sample stage 5 for changing the positional relationship between the sample and the charged particle optical column after placing the sample mounted to the sample support inside the case body 7 as described above. The aforementioned light-emitting member or the sample support including the light-emitting member is detachably arranged on the sample stage 5. A support panel 107 that functions as a bottom panel supported by the cover member 122 is attached, and the stage 5 is fixed to the support panel 107. The stage 5 is provided with an XY drive mechanism in an in-plane direction, a Z-axis drive mechanism in a height direction, and the like. The support panel 107 is attached so as to be directed to a facing surface of the cover member 122 and stretch toward the inside of the case body 7. Support shafts extend from the Z-axis drive mechanism and the XY drive mechanism, respectively and are connected to an operation grip 51 and an operation grip 52 included in the cover member 122, respectively. The user of the apparatus can adjust the position of the sample by operating the operation grips. In addition, a configuration is also applicable in which the optical microscope can be provided on the cover member 122 as will be described later.

It is possible to mount the sample support 600 provided with the detection element 500 on the sample stage 5. As described above, the detection element 500 transforms the charged particle beam into light. The light detector 503 for detecting the light, transforming the light into an electrical signal, and amplifying the signal is provided on the sample stage 5 or in the vicinity of the stage. As described above, the sample support provided with the detection element 500 may be located at a close position to the light detector or may be in contact with the light detector in order to efficiently detect the light signal. In addition, the light transmission path may be arranged therebetween. Although the light detector is provided on the sample stage in the drawing, the light detector 503 may be fixed to any location of the case body 7 or may be provided outside the case body 7. In a case in which the light detector 503 is provided outside the case body 7, the light detector can detect the light signal transformed by the detection element 500 by the light transmission path for delivering the light, such as glass or optical fiber, being located in the vicinity of the sample support 500 and the light signal being delivered through the light transmission path. The light detector is a semiconductor detection element or a photo-multiplier, for example. In any cases, the light detector according to the embodiment detects the light that is emitted by the detection element of the aforementioned sample support and passes through the transparent member.

The drawing illustrates a state in which the light detector 503 is provided on the stage 5. A preamplifier substrate 505 is connected from the light detector 503 provided on the stage 5 via wiring 504. The preamplifier substrate 505 is connected to the lower-order control unit 37 via wiring 507. Although the preamplifier substrate 505 is inside the case body 7 in the drawing, the preamplifier substrate 505 may be outside the case body 7. There is a projection 506 on the sample stage 5, and the sample support 600 is arranged by using the projection 506. In doing so, it is possible to fix the sample support 5 and prevent positional deviation. In addition, fixation to the sample support 600 can be made with a double-stick tape or the like on the stage 5. However, in the case in which the sample support according to the embodiment is used with the optical microscope as described above, it is not preferable to attach the double-stick tape to the lower surface of the sample support 600, and it is desirable to attach a positional deviation prevention member to the side surface or the like of the sample support 600 with a double-stick tape or the like. Since the light detector 503 is arranged immediately below the base 501 if the sample support 600 is mounted to the light detector 503, it is possible to efficiently detect the light that is transmitted through the sample 6 and is emitted by the detection element 500. By such an apparatus and a method, it is possible to obtain a transmission charged particle image by using the charged particle beam apparatus. Furthermore, in a case in which the sample support according to the embodiment is formed of a transparent member, it is possible to perform observation with the optical microscope after extracting the sample support to the outside of the charged particle beam apparatus.

In addition, since the charged particle beam apparatus according to the embodiment includes both the detector 3 and the detection element 500, it is possible to cause the detector 3 to obtain the secondary charged particles that are generated or reflected by the sample and to cause the detection element 500 to obtain the transmission charged particles that are transmitted through or scattered in the sample. Accordingly, it is possible to switch display of a secondary charged particle beam image and a transmission charged particle image on the monitor 35 by using the lower-order control unit 37 or the like. In addition, it is possible to display two kinds of images at the same time.

<Description of Observation with Charged Particle Beam Apparatus Under Atmospheric Pressure>

Next, a description will be given of a configuration in which the embodiment is applied to a charged particle beam apparatus capable of performing observation under an atmospheric pressure with reference to FIG. 18. The charged particle beam apparatus according to the embodiment is configured mainly of the charged particle optical column 2, the first case body (hereinafter, also referred to as a vacuum chamber) 7 that supports the charged particle optical column with respect to the apparatus installation surface, a second case body (hereinafter, also referred to as an attachment) 121 that is used in a state of being inserted into the first case body 7, the sample stage 5 that is arranged in the second case body, and a control system that controls the charged particle optical column 2, the first case body 7, the second case body 121, and the sample stage 5. Since basic configurations of the control system and the like are the same as those in FIG. 18, detailed descriptions thereof will be omitted.

At least one of side surfaces of a rectangular parallelepiped shape of the second case body 121 is an opened surface. The surfaces other than the surface, on which a barrier membrane holding member 155 is installed, among the side surfaces of the rectangular parallelepiped shape of a main body 121 are configured of walls of the second case body 121. Alternatively, the second case body 121 itself may be not provided with a wall and may be configured of side walls of the first case body 7 in a state of being assembled in the first case body 7. The second case body 121 is inserted into the first case body 7 through the opening portion and has a function of accommodating the sample 6 as a target of observation in a state of being assembled in the first case body 7. The first case body 7 and the second case body 121 are connected via a vacuum sealing member 126 and are fixed to an outer wall surface of the side surface side. The second case body 121 may be fixed to any of the side surface and the inner wall surface of the first case body 7 and the charged particle optical column. In doing so, the entire second case body 121 is fitted into the first case body 7. The aforementioned opening portion is most simply produced by utilizing an opening for carrying in and out the sample, which is originally provided in the vacuum sample chamber of the charged particle microscope. That is, if the second case body 121 is produced so as to match the size of the hole that is originally provided and the vacuum sealing member 126 is attached to the circumference of the hole, a modification of the apparatus can be minimized. In addition, the second case body 121 can be detached from the first case body 7.

The side surface of the second case body 121 is an opened surface that communicates with an atmospheric air space through a surface with at least a size that allows carrying in and out of the sample, and the sample 6 that is accommodated in the second case body 121 is maintained in an atmospheric pressure state, a slightly negatively pressurized state, or a desired gas type state during the observation. Although FIG. 18 is a sectional view of the apparatus in a direction parallel to the optical axis and only one opened surface is illustrated, the number of the opened surfaces of the second case body 121 is not limited to one as long as the vacuum sealing is established with the side surfaces of the first case body in the further direction and the closer direction of the paper in FIG. 18. It is only necessary that at least one or more opened surfaces are provided in the state in which the second case body 121 is assembled in the first case body 7. By the opened surfaces of the second case body, the sample can be carried in and out between the inside and the outside of the second case body (attachment).

A barrier membrane 10 through which the charged particle beam can be transmitted and pass is provided on the upper surface side of the second case body 121. The barrier membrane 10 can be attached to and detached from the second case body 121. The vacuum pump 4 is connected to the first case body 7 and evacuates a closed space (hereinafter, referred to as a first space) that is configured of the inner wall surface of the first case body 7, the outer wall surface of the second case body, and the barrier membrane 10. In doing so, the first space 11 is maintained in a highly vacuum state by the barrier membrane 10 while a second space 12 is maintained in a gas atmosphere at the atmospheric pressure or at substantially the same pressure as the atmospheric pressure in the embodiment. Therefore, it is possible to maintain the side of the charged particle optical column 2 in the vacuum state and to maintain the sample 6 and the aforementioned sample support at the atmospheric pressure or a predetermined atmospheric pressure during an operation of the apparatus. The barrier membrane 10 is held by the barrier membrane holding member 155, and exchange of the barrier membrane 10 can be achieved by exchanging the barrier membrane holding member 155.

In the case of the charged particle microscope according to the embodiment, the opened surface that configures at least one side surface of the second case body 121 can be covered with a cover member 122. The cover member 122 is provided with the sample stage and the like.

The charged particle microscope according to the embodiment has a function of supplying replacement gas to the inside of the second case body 121 and a function with which it is possible to form a pressure state that is different from that of the first space. The charged particle beam that is released from the lower end of the charged particle optical column 2 passes through the first space that is maintained at the highly vacuum state, passes through the barrier membrane 10 illustrated in FIG. 18, and further enters the second space that is maintained in the atmospheric pressure state or the slightly negatively pressurized state. That is, the second space is in a state in which a level of vacuum is lower than that in the first space (lower vacuum level). Since the charged particle beam is scattered by gas molecules in the atmospheric air space, the mean free path becomes short. That is, if the distance between the barrier 10 and the sample 6 is long, the primary charged particle beam, or the secondary charged particles, reflected charged particles, or transmission charged particles that are generated by irradiation with the primary charged particle beam do not reach the sample, the detector 3, and the detection element 500. In contrast, the probability of scattering of the charged particle beam is proportional to the mass number and density of gas molecules. Therefore, it is possible to lower the probability of scattering of the charged particle beam and cause the charged particle beam to reach the sample by replacing the second space with gas molecules with a smaller mass number than that of the atmospheric air or by slightly performing vacuuming. In addition, it is only necessary that the air in at least the path, through which the charged particle beam passes, in the second space, that is, the atmospheric air in the space between the barrier membrane and the sample instead of the air in the entire second space can be replaced with the gas. If nitrogen or water vapor that is gas lighter than the atmospheric air is employed as the type of the replacement gas, it is possible to observe an effect of improving S/N in an image. However, the effect of improving S/N in the image is higher when helium gas or hydrogen gas with smaller mass is used.

For the aforementioned reason, an attachment portion (gas introduction portion) of the gas supply tube 100 is provided in the cover member 122 in the charged particle microscope according to the embodiment. The gas supply tube 100 is coupled to a gas tank 103 at the coupling portion 102, and thereby introducing the replacement gas into the second space 12. A gas control valve 101 is arranged at a mid-way point of the gas supply tube 100 so as to be able to control the flow volume of the replacement gas flowing through the tube. Therefore, a signal line extends from the gas control valve 101 to the lower-order control unit 37, and the user of the apparatus can control the flow volume of the replacement gas on the operation screen that is displayed on a monitor of the computer 35. In addition, the gas control valve 101 may be opened and closed through manual operations.

Since the replacement gas is light element gas, the replacement gas is easily accumulated in the upper portion of the second space 12, and the air on the lower side thereof is not easily replaced. Thus, an opening that communicates between the inside and the outside of the second space is provided on the lower side than the attachment position of the gas supply tube 100 in the cover member 122. For example, the opening is provided at an attachment position of a pressure adjustment valve 104 in FIG. 18. In doing so, the atmospheric gas is pressed by the light element gas introduced from the gas introduction portion and is then discharged from the opening on the lower side. Therefore, it is possible to efficiently replace the inside of the second case body 121 with the gas. In addition, the opening may be made to also function as a rough exhaust port which will be described later.

There is a case in which the electron beam is greatly scattered even in the light element gas such as helium gas. In such a case, it is only necessary to replace the gas tank 103 with a vacuum pump. By slightly performing vacuum drawing, it is possible to bring the inside of the second case body into a significantly low vacuum state (that is, an atmosphere at a pressure that is close to the atmospheric pressure). For example, a vacuum exhaust port is provided in the second case body 121 or the cover member 122, and the inside of the second case body 121 is vacuum-exhausted once. Thereafter, the replacement gas may be introduced. Since it is only necessary to reduce atmospheric gas constituents remaining inside the second case body 121 to a predetermined amount or less, high-vacuum exhaust is not required, and rough exhaust is sufficient as the vacuum exhaust in this case.

However, in a case of observing a sample that contains moisture such as a biological sample, for example, moisture is evaporated from the sample that is placed in the vacuum state once, and the state thereof varies. Therefore, it is preferable to perform the observation before complete evaporation or to introduce the replacement gas directly from the air atmosphere as described above. By closing the aforementioned opening with the cover member after the introduction of the replacement gas, it is possible to effectively seal the replacement gas in the second space.

As described above, in the embodiment, it is possible to control the space where the sample is placed to an arbitrary level of vacuum from the atmospheric pressure (about $10^5$ Pa) to about $10^3$ Pa. According to a so-called low-vacuum scanning electron microscope in the related art, since an electron beam column communicates with a sample chamber, a pressure in the electron beam column varies in conjunction with a pressure in the sample chamber if the degree of vacuum in the sample chamber is lowered to obtain a pressure that is close to the atmospheric pressure, and it is difficult to control the sample chamber to the pressure from the atmospheric pressure (about $10^5$ Pa) to $10^3$ Pa. According to the embodiment, since the second space is separate from the first space with a thin film, it is possible to freely control the pressure and the gas type in the atmosphere in the second space that is surrounded by the second case body 121 and the cover member 122. Accordingly, it is possible to realize the control of the sample chamber to the pressure from the atmospheric pressure (about $10^5$ Pa) to $10^3$ Pa, which is difficult in the related art. Furthermore, it is possible to observe states of the sample while continuously varying the pressure to other pressures around the atmospheric pressure in addition to the observation at the atmospheric pressure (about $10^5$ Pa).

If a three-way valve is attached to the position of the opening, the opening can be made to function both as a rough exhaust port and as an exhaust opening for atmospheric air leakage. That is, it is possible to realize the exhaust opening that is made to function both as the rough exhaust port and as the exhaust opening by attaching one way of the three-way valve to the cover member 122, connecting another way thereof to the vacuum pump for rough exhaust, and attaching the leak valve to the other way.

The pressure adjustment valve 104 may be provided instead of the aforementioned opening. The pressure adjustment valve 104 functions so as to automatically open when the internal pressure of the second case body 121 becomes equal to or greater than 1 atm. By providing the pressure adjustment valve with such a function, it is possible to discharge the atmospheric gas constituents such as nitrogen and oxygen to the outside of the apparatus by automatically opening the pressure adjustment valve when the internal pressure becomes equal to or greater than 1 atm during introduction of the light element gas and to fill the inside of the apparatus with the light element gas. In addition, the gas tank or the vacuum pump 103 illustrated in the drawing is provided in the charged particle microscope in some cases, or the user of the apparatus attaches the gas tank or the vacuum pump 103 thereto later in other cases.

The sample support provided with the detection element 500 can be mounted to the sample stage 5 of the charged particle beam apparatus. In the state in which the aforementioned sample support is placed on the sample stage, the detection element 500 is in a state of being placed on the opposite side of the barrier membrane with respect to the sample. Arrangement configurations of the light detector 503 and the like in the vicinity of the sample stage are the same as those in FIG. 17. In the case of this configuration, it is possible to obtain a transmission charged particle beam signal in which variations in forms such as moisture evaporation that is caused by vacuum drawing are minimized. In addition, since it is not necessary to perform the vacuum drawing until the sample space becomes a highly vacuum state, it is possible to obtain a transmission charged particle beam microscope image of the sample on the sample support 600 at a significantly high throughput.

<Description of Observation with Optical Microscope>

FIG. 19 illustrates a case of performing observation with an optical microscope. First, a description will be given of an optical microscope 250. The optical microscope 250 is provided with optical lenses such as a field lens 252. Microscope information through the optical lens is projected to an ocular lens 207. Alternatively, the microscope information may be transformed into a digital signal by a CCD camera and may be displayed on a monitor which is not shown in the drawing. The sample support 600 according to the embodiment is arranged on a sample stage 258 that is provided with drive mechanisms 204 such as an XY drive mechanism that can be moved in the lateral direction in the drawing or in the paper plane direction with respect to an optical axis 251 of the optical microscope and a Z-axis drive mechanism that can change the distance from the field lens 252. An opening portion 259 is provided around the optical axis 251 of the optical microscope on the sample stage 258, and the sample support 600 according to the embodiment is arranged over the opening portion. The optical microscope 250 is provided with light sources that are capable of emitting white light, ultraviolet light, light with a controlled wavelength, or a photon beam such as a laser. The light sources include a light source 255 for emitting light from the upper side of the sample support 600 in the drawing and a light source 256 for emitting light from the lower side of the sample support 600. In addition, the light source may be a light source of a room where the optical microscope 250 is arranged or solar light. For the light source, supply and control are performed to adjust the light intensity of the light and the power source for turning on and off the light by a communication line, an electric line, or the like which is not shown in the drawing. Although the light sources are arranged at the aforementioned two locations in the drawing, at least one light source may be provided. Although the example of two light source locations was described above, the light sources may be arranged at other locations. In order to change an observation magnifying power or a focus position of the sample 6 on the sample support, the optical microscope 250 includes an optical lens drive mechanism 253. By moving the field lens 252 in a direction of the optical axis 251 of the optical microscope by the optical lens drive mechanism 253, it is possible to adjust the focal point on the sample 6 on the sample support 600. Although not shown in the drawing, the focal point may be changed by moving the optical lens inside the optical microscope 250 in the direction of the optical axis 251 instead of the field lens 252.

The light emitted from the light source 256 is released from the field lens 251 or a circumference thereof via a mirror or the like in the optical microscope 250 and reaches the sample support 600. The photon beam that has reached the sample support 600 passes through the base 501 and the detection element 500 and reaches the sample. Reflected light that has been reflected by the sample passes through the detection element 500 and the base 501 again and reaches the field lens 251. In doing so, an image is formed inside the optical microscope 251 from a signal of light with which the field lens 251 is irradiated, and the observation of the sample with the optical microscope can be performed through the ocular lens 207. In a case in which the light source position corresponds to the light source 255, the sample is irradiated with the photon beam released from the light source 255 first. It is possible to form the optical microscope image by causing the photon beam that has been transmitted through the sample to pass through the detection element 500 and the base 501 and pass through the field lens.

Although the optical microscope described with reference to the drawing is an inverted optical microscope in which the optical lens and the like are arranged below the sample, an upright optical microscope in which the optical system is arranged above the sample is also employed. In such a case, the light sources may be placed at any arbitrary locations.

The method and apparatus for observing the sample 6 on the sample support 600 according to the embodiment with the optical microscope was described hitherto. If the detection element 500 and the base 501 are transparent with respect to the light from the light sources as described above, it is possible to perform the observation with the optical microscope while transmitting light through the sample and the sample support, and also, it is possible to obtain a charged particle microscope image in vacuum or in the atmospheric air by the charged particle beam microscope apparatus as illustrated in FIGS. 17 and 18.

Second Embodiment

In the first embodiment, the configuration in which the light emitted by the detection element 500 passes through the detection element 500 and the sample support 600 and the light is detected below the detection element 500 or the sample support 600 was described. In this embodiment, configurations of a sample support and an apparatus in which the light generated by the detection element 500 is detected on the upper side or the lateral side of the detection element 500 or the sample support 600 will be described. Since portions that are not particularly stated in this embodiment, such as the material and the shape of the detection element 500 and provision of the layer for facilitating the adhesion of the sample to the detection element and the conductive film layer for removing the electrification due to the charged particle beam, are the same as those in the first embodiment, the detailed descriptions thereof will be omitted.

First, a description will be given of principles of light generation and emitted light detection with reference to FIG. 20. The sample 6 is made to adhere to or is in contact with the sample adhesion layer 812 on the detection element 500. Since the sample adhesion layer is the same as that in the first embodiment, a detailed description thereof will be omitted. The charged particle beam that has passed through the sample adhesion layer 812 enters the detection element 500, and the light emission 814 is caused. If the charged particle beam that has been transmitted through or scattered in the sample 6 reaches the detection element 500, ultraviolet light, visible light, infrared light, or the like is emitted. The wavelength of the emitted light may be any wavelength within a wavelength range that can be detected by the detector. Since the thickness B of the light-emitting region is the same as that in the first embodiment, a detailed description thereof will be omitted. If it is considered that the site 508 with high density and the site 509 with low density are present in the sample in the same manner as in the first embodiment, the charged particle beam can be transmitted up to the detection element 500 if the site 509 with low density in the sample is irradiated with the primary charged particle beam 511. The light 814 that is generated in the light-emitting region 813 with low density below the sample is released to the upper side in the drawing as well as the lower side in the drawing. That is, even if the charged particle beam is scanned and a light signal at the scanning position is obtained on the upper side than the sample, the obtained light signal is transmission information inside the sample 6 or a signal representing a transmission image. According to this principle, the region C that does not contribute to the light-emitting region in the detection element 500 is not necessarily transparent. Similarly, the sample support 600 is not necessarily transparent. For example, the sample support 600 may be a metal member made of aluminum, for example. In a case in which it is desired to perform observation with the light transmission optical microscope as described above in the first embodiment, it is only necessary to separate the detection element 500 from the sample support 600 and to use only the detection element 500. In such a case, it is necessary that the detection element 500 is as transparent as possible with respect to the light from the light transmission optical microscope used.

Since the light generated in the light-emitting region 813 is released in the lower direction in the drawing, a light reflective portion 815 may be provided between the light sample support 600 and the detection element 500 to reflect light and generate reflected light 816 in order to enhance a light detection rate. The light reflective portion 815 is configured by providing a light reflective film for reflecting light on the lower surface of the detection element 500, making the sample support 600 from metal polished for easily reflecting light, or arranging a metal film for reflecting light between the sample support 600 and the detection element 500. In such a case, it is desirable that the region B is transparent enough to deliver the emitted light while minimizing a loss. A detector instead of the light reflective portion 815 may also be provided on the lower side of the detection element 500 separately from the light detector 800, the light may be detected by these detectors together, and the detection signals may be synthesized.

According to the scheme of directly detecting the charged particle beam, the position of the detector for detecting the transmitted charged particle beam is limited at least to a position below the sample. However, by transforming the transmission charged particle beam into light and detecting the light as described above, a degree of freedom in relation to the detector installation position significantly increases, and it becomes possible to form a transmission charged particle beam image even from a signal from a detector in the lateral direction of the sample or in the upper direction than the sample. This is because the light generated by the transmission charged particle beam is omnidirectionally generated inside the light-emitting member as described above and the light can be detected regardless of the direction in which the detector is installed with respect to the sample. Specifically, the "lateral direction" of the sample means a position at which a horizontal surface where the sample is placed intersects a detection surface of the detector, and the "upper direction" of the sample means a position when the detection surface of the detector is above (on the side of the charged particle source) the horizontal surface where the sample is placed.

Next, an exemplary apparatus configuration according to the embodiment will be shown in FIG. 21. In FIG. 21, a configuration includes the charged particle optical column 2, the case body 7, the vacuum pump 4, the sample stage 5, the control system, and the like in the same manner as in FIG. 17. Since operations and functions of the respective elements and additional elements that are added to the respective elements are substantially the same as those in the first embodiment, detailed descriptions thereof will be omitted. In the case of the embodiment, the detection element 500 for detecting, as a light signal, the charged particle beam that has been transmitted through or scattered in the sample is arranged below the sample in the same manner as in the first embodiment. The detection element 500 is a light-emitting member capable of emitting light such as ultraviolet light, visible light, or infrared light when irradiated with the charged particle beam. The signal of the light emitted by the detection element 500 is detected by the detector 3 provided in the case body 7 or the light detector 800 that is capable of detecting light that has passed the light transmission path 801 for delivering light to the light detector 800. Although two detectors, namely the detector 3 and the light detector 800 are illustrated in the drawing, any one of or both the detectors may be provided. In addition, a detector for detecting the charged particle beam and the light may be arranged at another location and may be used to detect the light from the light-emitting member. For example, it is possible to use a detector that is arranged in the charged particle optical column instead of the aforementioned detectors or to use the detector in the charged particle optical column along with the aforementioned detectors. It is possible to obtain an internal transmission signal of the sample by the detector 3 or the light detector 800. Although not shown in the drawing, the light-emitting member 500 and the sample support or the stage may be fixed to each other by a double-stick tape or the like in order for the light-emitting member 500 not to drop from the sample support or the stage when the sample stage is moved. In a case in which it is desired to prevent contamination due to contact of the double-stick tape with the light-emitting member from occurring, a component for covering the side surface, the upper surface, or the like of the light-emitting member 500 may be provided as described above.

Hereinafter, a detailed description will be given of the detector 3. The detector 3 is a detector that is capable of detecting the light signal generated by the detection element 500, and for example, is a semiconductor detector that is made of a semiconductor material such as silicon. Since an electron-hole pair is generated when the light signal is incident on the semiconductor detector, the light signal is transformed into an electrical signal. The electrical signal is amplified by a signal amplification circuit 53 or the like and is displayed on the screen of the computer 35 as image information via the lower-order control unit 37 or the upper-order control unit 36 or is stored in a storage unit such as a memory or a hard disc. The semiconductor detector is configured of silicon or the like, and it is possible to produce the semiconductor detector to have a significantly thin thickness. Therefore, it is possible to arrange the semiconductor detector at a significantly narrow position between the charged particle optical column and the sample. Since resolution of an image increases as the distance between the charged particle optical column and the sample decreases in a case of a typical charged particle beam apparatus, for example, it is desirable to detect light by using the thin semiconductor detector 3 in a case in which it is desired to narrow the distance between the charged particle optical column and the sample.

Next, a description will be given of the light detector 800. The light detector 800 is a photomultiplier that is capable of transforming and amplifying the light signal into an electrical signal (photomultiplier). The light generated by the detection element 500 passes through the light transmission path 801 that can allow passing of the emitted light in the wavelength region and reaches the light detector 800 such as a light intensifier tube that is provided outside the case body 7. A material of the light transmission path 801 that allows the passing of the emitted light in the wavelength region is a material that is transparent or semi-transparent with respect to the light, such as quartz, glass, optical fiber, or plastic. In order to cause the light to easily reach the light detector 800 such as a photomultiplier, a light reflective material or the like may be arranged in the circumference of the light transmission path 801. The light which has reached the light intensifier tube is amplified and is transformed into an electrical signal. The electrical signal is amplified by the signal amplification circuit 802 or the like and is displayed on the screen of the computer 35 as image information via the lower-order control unit 37 or the upper-order control unit 36 or is stored in the storage unit such as a memory or a hard disc.

Figure 22A:
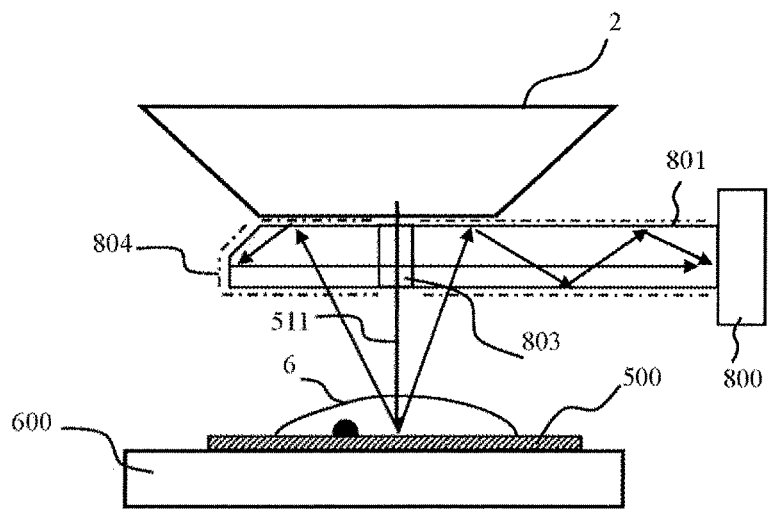
FIGS. 22A and 22B are a configuration diagram in a circumference of a detector according to the second embodiment.
Figure 22B:
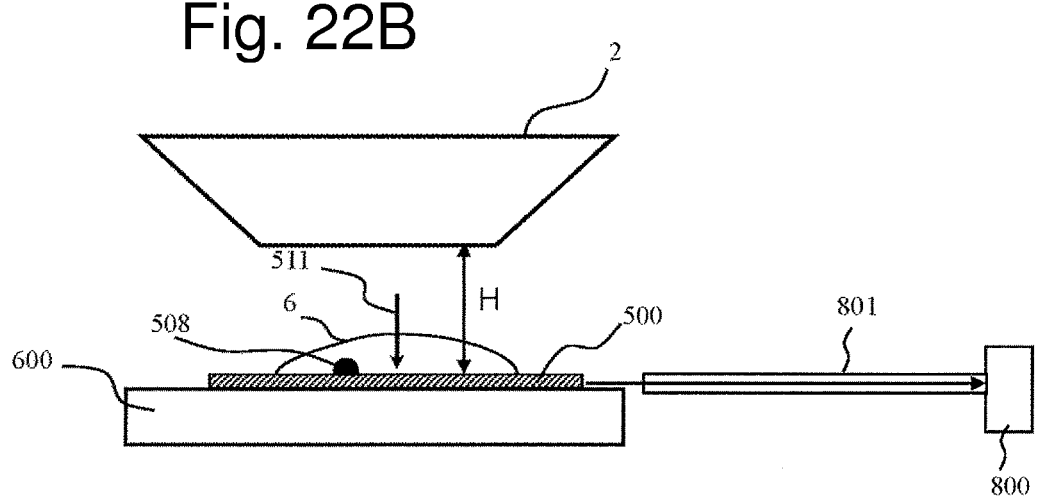

FIG. 22 illustrates another configuration of the light transmission path 801. In FIG. 22(*a*), the light transmission path 801 for delivering light is arranged between the charged particle optical column and the sample in order to efficiently collect the light. More specifically, the light transmission path 801 is provided immediately below the charged particle optical column, for example, below the field lens. The light transmission path 801 illustrated in the drawing is an annular light transmission path including a hole 803 provided at the center thereof so as to allow the primary charged particle beam to pass therethrough. The light transmission path 801 is provided with a light reflective material 804 (the one-dotted chain line in the drawing) for delivering the light to the side of the light detector 800 such as a photomultiplier in order for the light that has once entered the light transmission path 801 not to leak to the outside. In the case of this configuration, it is possible to collect the light emitted from the detection element 500 at a wide angle and to thereby more efficiently detect the light. In FIG. 22(b), the light transmission path 801 for delivering the light is provided immediately next to the detection element. The light transmission path 801 may be a flexible member such as an optical fiber. Since it is possible to cause the light transmission path 801 to approach the sample in this example, the light is significantly effectively collected. In addition, since resolution of an image increases as the distance between the charged particle optical column and the sample is shorter in the typical charged particle beam apparatus as described above, the configuration illustrated in FIG. 22(b) is preferably employed in a case in which it is desired to further narrow the distance between the charged particle optical column and the sample.

The light transmission path 801 may be arranged at a position other than the aforementioned position, and may be arranged on the lower side or the lateral side of the sample stage 5, or may be arranged in the charged particle optical column, for example. The light detector 800 such as a photoelectron amplifier may be inside or outside the case body 7 as long as the light transmission path 801 is used, and a degree of freedom in arranging the detector increases. In addition, it is not necessary to provide the light transmission path 801 as long as it is possible to arrange the light detector 800 such as a photomultiplier at a location that is relatively close to the sample. Positions and modification examples of the light amplifier and the light transmission paths belong to the scope of the charged particle beam microscope according to the embodiment as long as the light amplifier and the light transmission path satisfy the functions intended in the embodiment.

If the sample 6 is mounted on a sample support in the related art that does not emit light instead of the detection element 500 as a light-emitting member, the detector 3 can obtain the reflected charged particle beam that is reflected by the sample 6. That is, it is possible to obtain a sample transmission image if the platform to which the sample is mounted is changed to the light-emitting member, and it is possible to use the same apparatus as a typical charge particle beam apparatus if the platform to which the sample is mounted is changed to a non-light-emitting member. Accordingly, it is possible to easily obtain a transmission charged particle image by an apparatus such as a scanning electron microscope in the related art without performing a complicated operation of changing the apparatus or using an apparatus dedicated for observation with the transmission charged particles, by using the sample support according to the embodiment.

In a case in which the sample support according to the embodiment is used in the apparatus configuration illustrated in FIG. 21, the detector 3 simultaneously detects the charged particle beam reflected by the sample and the light from the light-emitting member of the sample support as described above. Therefore, in a case in which it is desired to detect only the reflected charged particles by the detection element 3, a light absorbing body for causing the surface of the detection element 3 to reflect or absorb the light so as not to allow the detection element 3 to detect the light from the light-emitting member of the sample support may be provided. Alternatively, in the case in which the detection element 3 is a semiconductor detection element, arrangement to control a position of a depletion layer, for example, can be made in order to lower detection sensitivity with respect to the light.

Although the description was given of the apparatus configuration in which the space in the case body 7 was significantly large with reference to FIG. 21, an apparatus configuration may be implemented based on a side entry scheme in which the sample and the sample support are introduced from a small region in the side surface of the case body 7 as illustrated in FIG. 23. Since the control system for controlling the respective optical lenses, the detection system for detecting the detection signal, the vacuum pump for exhausting from the inside of the case body 7 and the charged particle optical column 2, and the like are obvious, the descriptions thereof will be omitted. The light emitted from the detection element 500 below the sample 6 can be detected by the light detector that is arranged inside the case body 7 or the like. The light detector for detecting the light emitted from the detection element 500 may be arranged inside or outside the case body 7, on the sample support 7 or the sample stage 5, or at any position in the optical column 2 in the drawing, and positions and modification examples of the light amplifier and the light transmission path belong to the scope of the charged particle beam microscope according to the embodiment as long as the functions intended in the embodiment are satisfied.

In addition, the observation of the inside of the sample may be performed from various angles while the sample is inclined by providing a mechanism capable of inclining the sample in the sample stage 5 in the apparatus configuration as illustrated in FIG. 17, 21, or 23. Information of an inner structure that is obtained by continuously capturing or continuously observing images while continuously moving inclination of the sample or intermittently moving the inclination of the sample at a specific angle and computing such images by a control unit such as a computer may be saved or displayed as a tomography. The information of the inner structure may be saved in a storage unit such as a hard disc. With such a function, it is possible to recognize a three-dimensional structure inside the sample by observing a fine structure inside the sample from various angles. Alternatively, the tomography observation may be realized by providing, to the charged particle beam optical column 2, an optical lens capable of changing an angle at which the sample is irradiated with the charged particle beam from the charged particle beam optical column. Since it is not necessary to provide the sample inclining function to the sample stage 5 in this case, the apparatus configuration is simplified. In addition, stereoscopic observation of stereoscopically observing the sample may be performed by using the saved or displayed image. During the stereoscopic observation, two images that are captured at different angles may be used, an image obtained by overlapping images with different colors may be used, or a display unit such as a monitor capable of allowing three-dimensional observation may be made to perform three-dimensional display.

Third Embodiment

Description of Basic Apparatus Configuration

In the first embodiment, the usage of the same sample support 600 with the optical microscope and the charged particle beam microscope that are individually arranged was described. Hereinafter, a description will be given of a composite microscope apparatus configuration in which the optical microscope and the charged particle beam microscope are integrated. Although the light detection element 503 is arranged immediately below the sample support, the light detection element 503 may be arranged at any position as long as the light detection element 503 can detect light as described above.

First, a description will be given of an outline of this configuration with reference to FIG. 24. Since operations and functions of the respective elements and additional elements that are added to the respective elements are substantially the same as those in the first embodiment, detailed descriptions thereof will be omitted.

In this configuration, the optical microscope 250 is arranged inside the case body 7 of the charged particle beam microscope apparatus. The optical microscope 250 forms an optical microscope image with visible light, ultraviolet light, or infrared light in a specific or entire wavelength region that has passed through the transparent member of the aforementioned sample support. The optical microscope 250 is arranged on the support panel 107 that supports the sample stage 5 and has a configuration of performing observation from the lower side of the sample support 600. It is necessary to respectively adjust an optical axis 200 of the charged particle optical column 2 and the optical axis 251 of the optical microscope 250 in order to match the positions of the observation with the charged particle beam microscope and the optical microscope. Therefore, an optical axis adjustment mechanism 260 capable of changing the position of the optical microscope 250 is provided. Here, a state where the cover member 122 is provided with the optical axis adjustment mechanism 260 is illustrated. The cover member 122 is provided with an operation unit of the optical axis adjustment mechanism 260. The position of the optical microscope 250 is changed by causing the optical microscope 250 to slide along an upper or lateral side of a base 263 such as a guide or a rail by rotating the optical axis adjustment mechanism 260, for example. Although only one optical axis adjustment mechanism 260 is illustrated in the drawing, a plurality of optical axis adjustment mechanisms 260 may be provided since it is also necessary to move the optical axes in the direction vertical to the paper plane in the drawing.

The optical axis adjustment mechanism 260 may be provided only in the second case body according to another embodiment though not shown in the drawing. In such a case, the position of the optical microscope 250 is changed in a state in which the cover member 122 is drawn out. Since it is possible to adjust the respective optical axes with this configuration, it is possible to observe the sample 6 with the charged particle optical column 2 and to observe the same site based on an optical microscope image with the optical microscope 250. Since the sample stage 5 and the optical microscope 250 are independently arranged as illustrated in the drawing, the position of the optical microscope 250 is not changed even if the sample stage 5 is moved.

According to this configuration, the microscope information that has passed through the optical lens of the optical microscope is delivered to a CCD camera 254 arranged in the case body 7. The CCD camera 254 functions as a signal formation unit that transforms optical information into a digital signal such as electrical information. The image information that is transformed into the electrical information by the CCD camera 254 is delivered to the control unit or the like via a communication line 209 or a communication line 45 and is then displayed on the monitor. It is a matter of course that an imaging device other than the CCD camera may be provided. A wiring connection portion 208 capable of delivering the signal while establishing atmosphere insulation between the case body 7 and the outside of the apparatus is arranged in a space from the communication line 209 or the communication line 45. The image capturing unit may perform direct observation using the ocular lens 254 as illustrated in FIG. 19.

In addition, the light sources of the optical microscope may be provided in the microscope 250 as illustrated in FIG. 19 or may be arranged on the side of the charged particle optical column 2.

According to the charged particle beam microscope with this configuration, it is possible to obtain not only a reflected charged particle microscope image by the detector 3 but also a transmission charged particle beam microscope image by the detection element 500. The configuration in which the sample support 600 according to the embodiment is provided on the sample stage is the same as illustrated in FIG. 17.

Figure 25A:
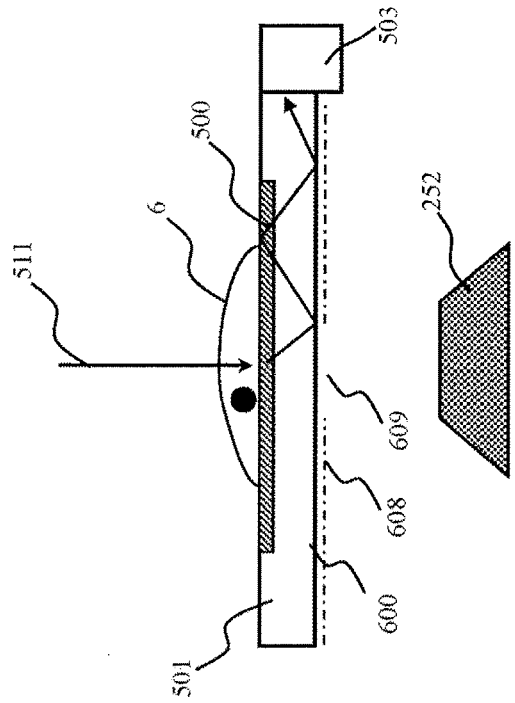
FIGS. 25A and 25B are an explanatory diagram for detecting a transmission charged particle beam from the detection element.
Figure 25B:
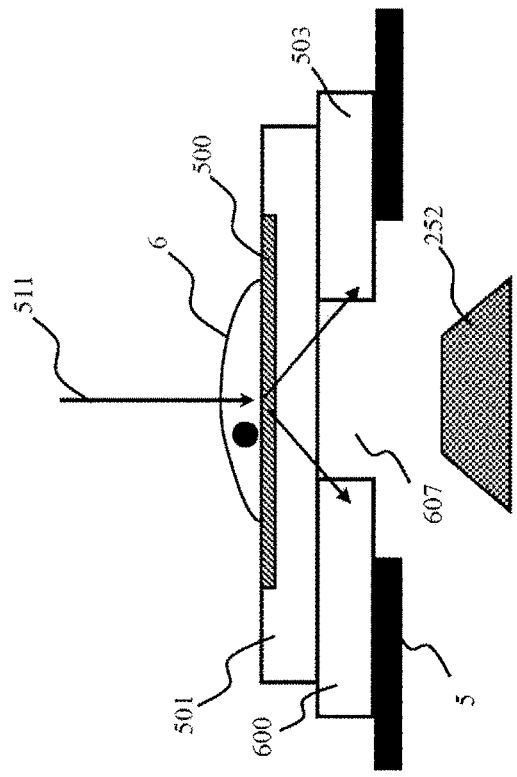

FIG. 25(*a*) illustrates a first configuration of a circumference of the sample support 600. In the case of this configuration, the light detector 503 with the opening portion 607 provided at the center thereof is arranged. In doing so, it is possible to arrange the field lens 252 of the optical microscope at a position near the sample support 600. By observing at least apart of the sample 6 on the sample support 600 through the opening portion, it is possible to perform observation with the optical microscope from the lower side of the drawing. Furthermore, it is possible to transform or amplify the light that is generated by irradiation of the detection element 500 with the charged particle beam that has been transmitted through the sample 6 into an electrical signal by the light detector 503 in the circumference of the opening portion 607.

FIG. 25(*b*) illustrates a second configuration. In such a case, the light detector 503 is provided on the lateral side of the sample support 600, and the light delivered through the inside of the sample support 600 is detected on the lateral side of the light detector 503. Since there is no light detector between the optical microscope and the sample support 600 as illustrated in FIG. 25(*a*) in this case, an optical microscope image with a wide field of view is easily obtained. Although not shown in the drawing, processing of reflecting light inside the sample support 600 may be performed in order to efficiently collect the light on the lateral side of the sample. For example, processing of performing light reflection treatment such as attachment of a reflective material or application of surface roughness to an upper surface, a lower surface, a side surface, or the like of the sample support 600 is performed. For example, light reflection treatment processing 608 is performed on the site as represented by the one-dotted chain line in FIG. 25(*b*). However, it is also necessary to provide an observation site 609 with no light reflection treatment processing performed thereon, such as a site to be observed with the optical microscope.

With such a configuration, it is possible to obtain the charged particle transmission signal generated by the charged particle beam apparatus and the light transmission signal generated by the optical microscope inside the same apparatus. Furthermore, it is possible to obtain the charged particle beam microscope image and the optical microscope image of the same site of the sample 6. By employing this configuration, it is possible to omit time and effort to alternately place the sample support 600 in the optical microscope 250 and the charged particle microscope apparatus 601 as illustrated in FIG. 1 and to perform observation with the optical microscope 250 and the charged particle microscope apparatus 601 by a single operation.

Furthermore, since the charged particle beam apparatus according to the embodiment is provided with the detector 3, it is possible to obtain, by the detector 3, the secondary charged particles that are generated or reflected by the sample, to obtain the transmission charged particles that have been transmitted through or scattered in the sample due to the light emitted by the detection element 500, and to obtain the optical microscope image by the optical microscope. Since these images can be obtained at the same time, it is possible to switch display of the secondary charged particle image, the transmission charged particle image, and the optical microscope image on the monitor 35 by using the lower-order control unit 37 or the like. In addition, it is also possible to display the three types of images at the same time. Although not shown in the drawing, the light transmission path 801, the light detector 800 such as a photoelectron amplifier, and the like may be arranged in the case body 7.

Although it is possible to observe the sample 6 with the optical microscope and the charged particle microscope without moving the sample stage 5 in the case illustrated in FIG. 24, the circumference of the sample stage has a significantly complicated structure. Thus, a configuration is also applicable in which the optical microscope 250 and the charged particle optical column 2 are aligned as illustrated in FIG. 26. The case body 7 is provided with the charged particle optical column 2 and the optical microscope 250. Since the sample stage 5, the vacuum pump, the detector, the display unit for displaying images, and the control system for controlling the optical lens and the like are obvious, depiction thereof is omitted. The light source 256 for obtaining an optical microscope image may be provided on the upper side or the lower side of the sample support 600. However, in the case in which the light source 256 is provided on the lower side of the sample support, it is necessary that the sample support 600 is transparent with respect to the light that is generated by the light source 256. If the light source 256 is provided on the upper side, the sample support 600 is not necessarily transparent. In the case of this configuration, it is possible to obtain the transmission charged particle image of the sample 6 and to cause the optical microscope 250 to obtain light information of the sample 6 by detecting the light emitted from the detection element 500 by the same apparatus. Since the positional relationship between the charged particle optical column 2 and the optical microscope 250 is maintained constant, it is possible to easily shift the transmission charged particle image and the optical microscope image by causing the control unit of the sample stage 5 or the upper-order control unit to memorize the positional relationship.

Fourth Embodiment

It is also possible to combine an atmospheric pressure charged particle beam microscope apparatus capable of performing observation under the atmospheric pressure and an optical microscope apparatus and to use the sample support according to the embodiment with the composite apparatus. The configuration will be illustrated in FIG. 27. Since these apparatuses basically have apparatus configurations as a combination of FIGS. 18 and 24, the repeated description of the aforementioned first to third embodiments will be omitted.

The configuration is characterized in that the aforementioned sample support is arranged between the charged particle optical microscope apparatus capable of performing observation under the atmospheric pressure and the optical microscope 250 under the atmospheric pressure. It is preferable to employ the apparatus configuration according to the embodiment when it is desired to obtain a transmission charged particle microscope image and an optical microscope image of the same site of a sample that contains a large amount of liquid.

Since it is not necessary to maintain the sample space in the highly vacuum state in the apparatus according to the embodiment, it is possible to carry in and out the sample at a significantly high throughput. In addition, it is possible to set a desired gas type and a pressure inside the second case body 7 as described above and to thereby perform observation with the transmission charged particle microscope and the optical microscope in desired gas.

Fifth Embodiment

In this embodiment, an example in which the second case body 121 is not provided unlike the aforementioned embodiments will be described. Since configurations of the circumference of the barrier membrane 10, the sample stage 5, and the circumference of the optical microscope 250 are substantially the same as those in the aforementioned first to fourth embodiments, differences will be mainly described below.

FIG. 28 illustrates an overall configuration of the charged particle microscope according to the embodiment. In the configuration, the charged particle optical column 2 is fitted into the case body 271 and is sealed in the vacuum state with the vacuum sealing member 123. The case body 271 is supported by a pillar 269. The pillar 269 is supported by a base 270. Although only one pillar 269 is illustrated in the drawing, it is preferable to provide a plurality of pillars 269 to support the case body in practice. Since an atmosphere state of the sample 6 becomes the same as that outside the apparatus with this configuration, it is possible to expose the sample to a state in a completely atmospheric air.

Gas supply from the gas tank 103 is performed by a gas nozzle 272 that is directed toward the direction to the vicinity of the sample 6. The gas nozzle 272 is connected to the case body 271 via a support 273, for example. The gas tank 103 is connected to the gas nozzle 272 via a coupling portion 102. Although the aforementioned configuration is an exemplary configuration, it is possible to eject desired gas to the vicinity of the sample 6 with this configuration. As a type of the gas, nitrogen, water vapor, helium gas, hydrogen gas, or the like that is lighter than the atmospheric air is employed in order to reduce scattering of the electron beam. The gas can be freely changed by the user. In addition, the gas tank 103 may be replaced with a vacuum pump in order to perform vacuum drawing between the barrier membrane 10 and the sample 6.

The optical microscope 250 is arranged immediately below the case body 271, that is, the optical microscope 250 is arranged coaxially with the optical axis of the charged particle optical column. In doing so, it is possible to obtain the charged particle beam microscope image by irradiating the sample 6 on the sample support 600 that is arranged on the sample stage 5 with the charged particle beam that has passed through the barrier membrane 10 and to obtain the optical microscope image generated by the optical microscope 250. Configurations of the optical axis adjustment mechanism 260, the optical lens drive mechanism 253 for driving the inner lens of the optical microscope in the direction of the optical axis 251 of the optical microscope 250, and the like are the same as those described in the aforementioned embodiments.

With the configuration according to the embodiment, it is possible to observe the same site with the charged particle beam microscope and the optical microscope in a state in which the barrier membrane 10, the sample 6, and the optical microscope 250 are in a non-contact state.

Since the sample arrangement space is not limited in the case of this configuration, the configuration is useful when the size of the sample support 600 is significantly large.

Sixth Embodiment

Next, an example will be shown in which an atmospheric pressure charged particle beam microscope apparatus capable of performing observation under the atmospheric pressure and an optical microscope apparatus are combined. In this embodiment, a description will be given of a configuration in which the charged particle optical column 2 according to the aforementioned embodiment is arranged on the lower side of the barrier membrane 10.

FIG. 29 illustrates a configuration diagram of the charged particle microscope according to the embodiment. The vacuum pump, the control system, and the like are omitted in the drawing. In addition, it is assumed that the case body 7 as a vacuum chamber and the charged particle optical column 2 are supported by a pillar, a support, or the like with respect to the apparatus installation surface. Operations and functions of the respective elements and additional elements that are added to the respective elements are substantially the same as those in the aforementioned embodiments, the detailed descriptions thereof will be omitted.

In order to maintain the sample 6 that is mounted to the sample support 600 and the barrier membrane 10 in the non-contact state, a sample stage 5 is provided on the barrier membrane holding member or the case body. That is, the lower portion of the sample 6 in the drawing is irradiated with the charged particle beam. By using the operation unit 204 for operating the sample stage 5, it is possible to cause the lower surface of the sample in the drawing to approach the barrier membrane 10 or to bring the lower surface thereof into contact with the barrier membrane 10.

In addition, the optical microscope 602 is arranged on the upper side of the charged particle optical column 2 and the sample support 600 and is arranged coaxially with the optical axis of the charged particle optical column. In doing so, it is possible to obtain the charged particle beam microscope image by irradiating the sample 6 that is arranged on the sample stage 5 with the charged particle beam that has passed through the barrier membrane 10 and to obtain the optical microscope image generated by the optical microscope 602 from the upper side in the drawing.

Seventh Embodiment

FIG. 30 illustrates a configuration in which the optical microscope is removed from the apparatus according to the fifth embodiment. Since the optical microscope is not provided in the case of the configuration, the opening portion 607 at the center of the light detector 503 is not necessarily provided. In a case in which it is desired to perform observation with a separately arranged optical microscope, it is only necessary to remove the sample support 501 from the sample stage 5 and to arrange the sample support 501 in the optical microscope. Since the light is detected in a space outside the apparatus in the case of this configuration, light from the outside, such as room light, is detected by the light detector 503 in some cases. Therefore, the light from the outside of the apparatus may be blocked by a cover or the like which is not illustrated in the drawing. Although the light detector 503 is arranged below the sample support 501 in the drawing, the light detector 503 may be arranged in the vacuum space 11. Since the optical microscope is not provided in the case of this configuration, apparatus cost becomes more reasonable.

Eighth Embodiment

Figure 31A:
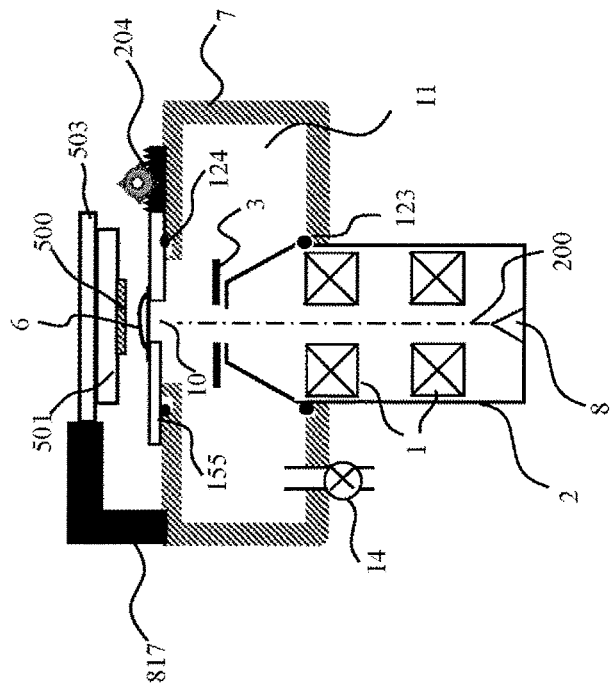
FIGS. 31A and 31B are a configuration diagram of a charged particle beam microscope according to an eighth embodiment.
Figure 31B:
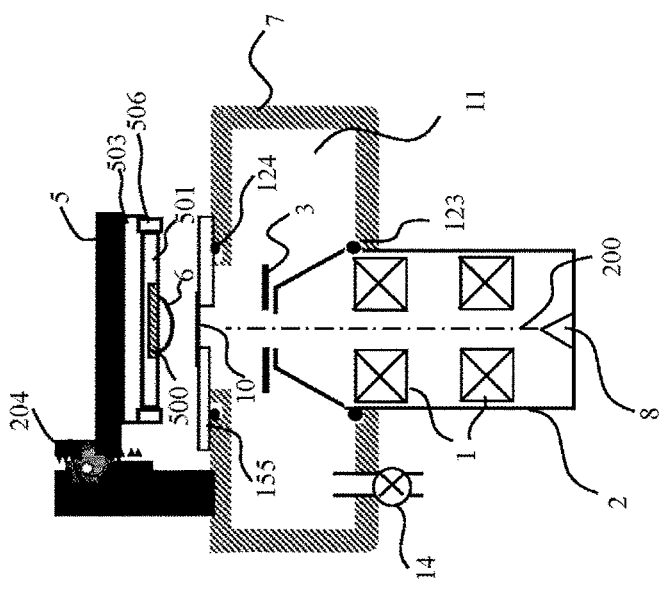

FIG. 31 illustrates a configuration in which the optical microscope is removed from the apparatus according to the sixth embodiment. Since the optical microscope is not provided in this configuration, the opening portion 607 at the center of the light detector 503 is not necessarily provided. FIG. 31(a) illustrates a state in which the sample 6 is in close contact with the detection element 500. In the case of this configuration, it is possible to move relative positions between the sample 6 and the barrier membrane 10 by moving the sample stage 5 by the drive mechanism 204. In addition, the sample 6 and the barrier membrane 10 may be brought into contact with each other or may be maintained in a non-contact state. In the case of bringing the sample 6 into contact with the barrier membrane 10, it is only necessary to cover the sample 6 with the light-emitting member 500. FIG. 31(b) illustrates a state in which the sample 6 is arranged on the barrier membrane 10 and the detection element 500, the light detector 503, and the like are provided in a support. Although not shown in the drawing, the detection element 500 and the light detector 503 may be provided with drive mechanisms capable of realizing motion in the vertical direction and the horizontal direction in the drawing. It is possible to change the relative positions between the sample 6 and the optical axis 200 by the barrier membrane holding member 155, the barrier membrane 10, and the drive mechanism 204 that is connected to the sample 6 mounted to the barrier membrane 10. The distance between the sample 6 and the light-emitting member 500 is adjusted to a desired distance, and the sample 6 and the light-emitting member 500 are arranged via a desired member such as atmospheric gas or desired gas that is introduced from the outside. In doing so, the charged particle beam that has been transmitted through the sample 6 mounted to the barrier membrane passes through the predetermined distance, and the light-emitting member 500 is irradiated with the charged particle beam via the gas member of the desired material. Therefore, it is possible to observe the sample 6 that is mounted to the barrier membrane 10 with the transmission charged particle microscope. Although not shown in the drawing, the sample 6 and the light-emitting member 500 may be in close contact with each other. Since the light is detected in the space outside the apparatus in the case of this configuration, the light such as room light is detected by the light detector 503 in some cases. Therefore, the light from the outside of the apparatus may be blocked by a cover or the like which is not shown in the drawing. Although the light detector 503 is above the sample support 501 in the drawing, the light detector 503 may be provided inside the vacuum space 11. Since the optical microscope is not provided in the case of this configuration as compared with the sixth embodiment, the apparatus cost becomes more reasonable.

The present invention is not limited to the aforementioned embodiments and includes various modification examples. For example, the aforementioned embodiments are for detailed descriptions of the present invention for the purpose of easy understanding, and the present invention is not necessarily limited to a structure including all the aforementioned configurations. It is possible to replace a part of a configuration according to a specific embodiment with a configuration according to another embodiment, or to add a configuration according to another embodiment to a configuration according to a specific embodiment. In relation to a part of a configuration according to each embodiment, addition, deletion, and replacement of another configuration can be made. Moreover, apart or entirety of the aforementioned respective configurations, functions, processing units, processing means, and the like can be realized as hardware by designing the part or the entirety thereof on an integrated circuit, for example. In addition, the aforementioned respective configurations, functions, and the like may be realized as software by a processor interpreting and executing programs for realizing the respective functions.

Information of programs, tables, files, and the like for realizing the respective functions can be stored in a memory, a recording device such as a hard disc or an SSD (Solid State Drive) or a recording medium such as an IC card, an SD card, or an optical disc.

In addition, only the control line and the information line that are considered to be necessary for the description were illustrated, and all the control lines and information lines in a product are not necessarily illustrated. It may be considered that substantially all the configurations are connected to each other in practice.

REFERENCE SIGNS LIST

1: optical lens
2: charged particle optical column
3: detector
4: vacuum pump
5: sample stage
6: sample
7: case body
8: charged particle source
10: barrier membrane
11: first space
12: second space
14: leak valve
15: opened surface
16: vacuum piping
17: stage support platform
18: support pillar
19: support member for cap member
20: bottom panel
35: computer
36: upper-order control unit
37: lower-order control unit
43, 44, 45: communication line
53: signal amplification circuit
100: gas supply tube
101: gas control valve
102: connecting portion
103: gas tank or vacuum pump
104: pressure adjustment valve
107: support panel
108: operation grip
109: operation grip
121: second case body
122: cover member
123, 124, 125, 126, 128, 129: vacuum sealing member
154: signal amplifier
155: holding member
156, 157, 158: signal line
159: barrier membrane holding base
200: optical axis of charged particle beam
204: drive mechanism
207: ocular lens
208: electric connection portion
209: wiring
250: optical microscope
251: optical axis of optical microscope
252: field lens
253: optical lens drive mechanism
254: CCD camera
255, 256, 257: light source
258: sample stage
259: opening portion
260: optical microscope position adjustment mechanism
263: base, rail, or guide
267: fine particle sample
268: connecting portion
269: pillar
270: base
271: case body
272: nozzle
273: support
274: support
500: detection element
501: base
502: thin film
503: light detector
504: side wall
505: preamplifier substrate
506: projection
507: wiring
508: portion with high density
509: portion with low density
510: primary charged particle beam
511: primary charged particle beam
600: sample support
601: charged particle beam microscope
602: optical microscope
603: light source
604: charged particle beam detector
606: optical axis of optical microscope
607: opening portion
608: light reflective portion
609: observation site
700: container
701: culture medium
800: light detector
801: light transmission path
802: signal amplification circuit
803: hole
804: light reflective material
805: base
806: culture solution
807: cultured cell
808: culture container
809: light reflective material
810: light reflective material
811: light transmission path
812: sample adhesion layer
813: light-emitting region
814: light emission
815: light reflective portion
816: reflected light
817: support

The invention claimed is:
1. A charged particle beam apparatus comprising:
a charged particle optical column that irradiates a sample with a primary charged particle beam;
a light-emitting member that is outside of the sample and disposed on a side of the sample opposite from the charged particle optical column and that transforms the primary charged particle beam transmitted through the sample or scattered in the sample into light and emits the light;

a sample stage on which a sample support that includes the light-emitting member is detachably arranged, wherein the light-emitting member is disposed between, and in contact with, the sample and the sample support, and the light-emitting member is disposed in a recess in an upper portion of the sample support such that an upper surface of the light-emitting member is coplanar with an upper surface of the sample support; and a detector that detects the light emitted by the light-emitting member.

2. The charged particle beam apparatus according to claim 1, further comprising:

a control unit that generates a transmission charged particle image of the sample in response to a signal from the detector.

3. The charged particle beam apparatus according to claim 1, further comprising:

a case body that accommodates the sample, wherein the detector is provided in at least one of the charged particle optical column and the case body.

4. The charged particle beam apparatus according to claim 1, wherein the detector is a photomultiplier.

5. The charged particle beam apparatus according to claim 4, wherein a light transmission path that delivers the light emitted by the light-emitting member is provided between the light-emitting member and the detector.

6. The charged particle beam apparatus according to claim 4, wherein a light transmission path that delivers the light emitted by the light-emitting member is provided between the charged particle optical column and the sample, and wherein the light transmission path includes a hole that is capable of allowing the primary charged particle beam to pass therethrough.

7. The charged particle beam apparatus according to claim 1, wherein the detector is a semiconductor detector that is provided between the charged particle optical column and the sample.

8. A sample observation method for observing a sample by irradiation with a primary charged particle beam of a charged particle beam apparatus that includes a charged particle optical column that irradiates the sample with the primary charged particle beam; a light-emitting member that is outside of the sample and disposed on a side of the sample opposite from the charged particle optical column and that transforms the primary charged particle beam transmitted through the sample or scattered in the sample into light and emits the light; a sample stage on which a sample support that includes the light-emitting member is detachably arranged, wherein the light-emitting member is disposed between, and in contact with, the sample and the sample support, and the light-emitting member is disposed in a recess in an upper portion of the sample support such that an upper surface of the light-emitting member is coplanar with an upper surface of the sample support; and a detector that detects the light emitted by the light-emitting member, the method comprising:

a step of irradiating, with the charged particle beam, the sample that is arranged on the light-emitting member, which forms at least a part of the sample support and emits light by charged particles that have been transmitted through or scattered in the sample, directly or via a predetermined member; and a step of obtaining a charged particle beam microscope image by detecting the light that is emitted by the light-emitting member and is directed to an outside of the sample support.

9. The sample observation method according to claim 8, wherein the sample is a biological sample, and the method further comprises:

a step of arranging the sample on the light-emitting member directly or via a predetermined member by at least a step of arranging a culture medium that includes a nutritional material in a form of solid, liquid, or gas on the light-emitting member along with the sample, and a step of culturing or cultivating the sample on the light-emitting member.

10. The sample observation method according to claim 8, further comprising:

a step of arranging the sample on the light-emitting member directly or via a predetermined member by at least a step of arranging the sample in a liquid, and a step of causing the liquid to adhere to the light-emitting member.

11. The sample observation method according to claim 8, further comprising:

a step of arranging the sample on the light-emitting member directly or via a predetermined member by at least a step of splitting the sample into pieces, and a step of mounting a split piece of the sample to the light-emitting member.

12. A sample support to which a sample to be observed by irradiation with a charged particle beam is mounted, comprising:

a light-emitting member that forms at least a part of the sample support, is outside of the sample and disposed on a side of the sample opposite from a charged particle optical column that irradiates the sample with a primary charged particle beam, and transforms the primary charged particle beam transmitted through or scattered in the sample into light and emits the light, wherein the sample support is detachably arranged on a sample stage, wherein the light-emitting member is disposed between, and in contact with, the sample and the sample support, and the light-emitting member is disposed in a recess in an upper portion of the sample support such that an upper surface of the light-emitting member is coplanar with an upper surface of the sample support, and wherein the light emitted by the light-emitting member is directed to the outside of the sample support.

13. The sample support according to claim 12, wherein the sample is arranged on the light-emitting member directly or via a predetermined member.

14. The sample support according to claim 12, wherein the light emitted by the light-emitting member is in a specific or arbitrary wavelength region among those of visible light, ultraviolet light, and infrared light.

15. The sample support according to claim 12, further comprising:
a reflective material that reflects the light generated by the light-emitting member.

16. The sample support according to claim 12,
wherein the sample support includes at least a portion with a concave shape, and the sample is arranged in a concavity of the concave shape.

17. The sample support according to claim 12, further comprising:
an electrification prevention member that is provided on a surface on which the sample is placed in order to prevent electrification of the sample.

18. The sample support according to claim 12,
wherein the surface on which the sample is placed is coated with a material for enhancing adhesiveness between the sample support and the sample.

19. The sample support according to claim 18,
wherein the material for enhancing the adhesiveness between the sample support and the sample is a molecule in a positively charged state.

20. An observation system comprising:
a charged particle optical column that irradiates a sample with a primary charged particle beam;
a light-emitting member that is disposed on a side of the sample opposite from the charged particle optical column and that transforms the primary charged particle beam transmitted through the sample or scattered in the sample into light and emits the light;
a sample stage on which a sample support is detachably arranged, the light-emitting member being disposed in a recess in the sample support, such that the light-emitting member is in contact with the sample and the sample support and an upper surface of the light-emitting member is coplanar with an upper surface of the sample support; and
a detector that detects the light emitted by the light-emitting member.

21. A charged particle beam apparatus comprising:
a charged particle optical column that irradiates a sample with a primary charged particle beam that is generated by a charged particle beam source;
a light-emitting member that is disposed outside of the sample and on a side of the sample opposite from the charged particle optical column and that transforms the primary charged particle beam transmitted through the sample or scattered in the sample into light and emits the light;
a sample stage on which a sample support for placing the sample thereon is arranged, wherein the light-emitting member is disposed between, and in contact with, the sample and the sample support, and the light-emitting member is disposed in a recess in an upper portion of the sample support such that an upper surface of the light-emitting member is coplanar with an upper surface of the sample support;
a detector that is arranged in a lateral direction of the sample or on a side of the charged particle beam source beyond the sample; and
a control unit that generates a transmission charged particle image of the sample in response to a signal that is detected by the detector.

22. The charged particle beam apparatus according to claim 1, wherein the detector is arranged on the sample stage below the sample support.

23. The observation system according to claim 20, wherein the detector is arranged on the sample stage below the sample support.

* * * * *